US012799157B2

(12) United States Patent
Song et al.

(10) Patent No.: US 12,799,157 B2
(45) Date of Patent: Nov. 17, 2026

(54) METHOD FOR PURIFYING BIOLOGICALLY ACTIVE PEPTIDE BY USING PROTEIN A AFFINITY CHROMATOGRAPHY

(71) Applicant: ABL BIO INC., Gyeonggi-do (KR)

(72) Inventors: Daehae Song, Gyeonggi-do (KR); Youngdon Pak, Gyeonggi-do (KR); Jinwon Jung, Gyeonggi-do (KR); Junghyeon Hong, Gyeonggi-do (KR); Heejin Lim, Gyeonggi-do (KR); Dongin Kim, Gyeonggi-do (KR)

(73) Assignee: ABL BIO INC., Seongnam-Si (KR)

( * ) Notice: Subject to any disclaimer, the term of this patent is extended or adjusted under 35 U.S.C. 154(b) by 1182 days.

(21) Appl. No.: 17/789,163

(22) PCT Filed: Dec. 24, 2020

(86) PCT No.: PCT/IB2020/062434
§ 371 (c)(1),
(2) Date: Jun. 24, 2022

(87) PCT Pub. No.: WO2021/130717
PCT Pub. Date: Jul. 1, 2021

(65) Prior Publication Data

US 2023/0212217 A1 Jul. 6, 2023

Related U.S. Application Data

(60) Provisional application No. 62/953,685, filed on Dec. 26, 2019, provisional application No. 62/953,687, filed on Dec. 26, 2019.

(30) Foreign Application Priority Data

Dec. 11, 2020 (KR) ........................ 10-2020-0173808

(51) Int. Cl.
*G01N 31/00* (2006.01)
*C07K 1/22* (2006.01)
*G01N 33/53* (2006.01)

(52) U.S. Cl.
CPC ..................................... *C07K 1/22* (2013.01)

(58) Field of Classification Search
None
See application file for complete search history.

(56) References Cited

U.S. PATENT DOCUMENTS

| | | | | |
|---|---|---|---|---|
| 8,586,713 | B2 * | 11/2013 | Davis | C07K 16/248 530/387.3 |
| 8,858,941 | B2 | 10/2014 | Gurney et al. | |
| 9,248,181 | B2 | 2/2016 | de Kruif et al. | |

FOREIGN PATENT DOCUMENTS

| | | | |
|---|---|---|---|
| JP | 2016-538275 | A | 12/2016 |
| JP | 2018-520089 | A | 7/2018 |
| KR | 10-2015-0076172 | A | 7/2015 |
| KR | 10-2016-0090308 | A | 7/2016 |
| KR | 10-2017-0035941 | A | 3/2017 |
| KR | 10-2017-0139131 | A | 12/2017 |
| WO | 2018/128454 | A1 | 7/2018 |
| WO | 2019/117684 | A1 | 6/2019 |

OTHER PUBLICATIONS

Ollier et al. (MABS, 2019, vol. 11, No. 8, pp. 1464-1478) (Year: 2019).*
International Search Report issued in corresponding International Patent Application No. PCT/IB2020/062434 dated Mar. 31, 2021.
Ollier et al., "Single-step Protein A and Protein G avidity purification methods to support bispecific antibody discovery and development", MABS, vol. 11, No. 8, 2019, pp. 1464-1478.

* cited by examiner

*Primary Examiner* — Lisa V Cook
(74) *Attorney, Agent, or Firm* — Morgan, Lewis & Bockius LLP

(57) ABSTRACT

Provided is a method of purifying a mixture of Fc-containing bioactive peptides by using an affinity column including an affinity matrix containing a protein A ligand, wherein the mixture of Fc-containing bioactive peptides includes a first Fc-containing bioactive peptide and a second Fc-containing bioactive peptide, and the second Fc-containing bioactive peptide includes at least one more human VH3 domain, compared to the first Fc-containing bioactive peptide. According to the purification method, bioactive peptides having the same or similar structures can be precisely separated to the high level of purity while simplification of the process is achieved.

19 Claims, 19 Drawing Sheets

Specification includes a Sequence Listing.

| Peak No. | Theoretical Molecular Weight (Da) | Experimental Molecular Weight (Da) |
|---|---|---|
| Peak 1 | 144410 | 144422 |
| Peak 2 | 171351 | 171367 |
| Peak 3 | 147077 | 147083 |
| Peak 4 | 173990 | 173998 |

SEQUENCE LISTING

```
<160> NUMBER OF SEQ ID NOS: 37

<210> SEQ ID NO 1
<211> LENGTH: 121
<212> TYPE: PRT
```

```
<213> ORGANISM: Artificial Sequence
<220> FEATURE:
<223> OTHER INFORMATION: H Variable region 1564

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Cys Leu Glu Trp Val
        35                  40                  45

Ser Ala Ile Ser Tyr Asp Asn Ala Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Val Leu Thr Thr Leu Met Asn Trp Phe Asp Tyr Trp Gly
            100                 105                 110

Gln Gly Thr Leu Val Thr Val Ser Ser
        115                 120


<210> SEQ ID NO 2
<211> LENGTH: 110
<212> TYPE: PRT
<213> ORGANISM: Artificial Sequence
<220> FEATURE:
<223> OTHER INFORMATION: L Variable region 1564

<400> SEQUENCE: 2

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

Asp Val Ser Trp Tyr Gln Gln Leu Pro Gly Thr Ala Pro Lys Leu Leu
        35                  40                  45

Ile Tyr Ala Asn Val Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Asp Ser Leu
                85                  90                  95

Asn Ala Tyr Val Phe Gly Cys Gly Thr Lys Leu Thr Val Leu
            100                 105                 110


<210> SEQ ID NO 3
<211> LENGTH: 121
<212> TYPE: PRT
<213> ORGANISM: Artificial Sequence
<220> FEATURE:
<223> OTHER INFORMATION: H Variable region F06

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Cys Leu Glu Trp Val
        35                  40                  45
```

```
Ser Ala Ile Ser Tyr Asp Asn Ala Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Val Leu Thr Thr Leu Met Asn Trp Phe Asp Tyr Trp Gly
            100                 105                 110

Gln Gly Thr Leu Val Thr Val Ser Ser
        115                 120


<210> SEQ ID NO 4
<211> LENGTH: 110
<212> TYPE: PRT
<213> ORGANISM: Artificial Sequence
<220> FEATURE:
<223> OTHER INFORMATION: L Variable region F06

<400> SEQUENCE: 4

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

Asp Val Ser Trp Tyr Gln Gln Leu Pro Gly Thr Ala Pro Lys Leu Leu
        35                  40                  45

Ile Tyr Ala Asn Val Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Ala Gly Ser Leu
                85                  90                  95

Asn Ala Tyr Val Phe Gly Cys Gly Thr Lys Leu Thr Val Leu
            100                 105                 110


<210> SEQ ID NO 5
<211> LENGTH: 121
<212> TYPE: PRT
<213> ORGANISM: Artificial Sequence
<220> FEATURE:
<223> OTHER INFORMATION: H Variable region VH5

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Cys Leu Glu Trp Val
        35                  40                  45

Ser Ala Ile Ser Gly Asp Asn Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Val Leu Thr Thr Leu Met Asn Trp Phe Asp Ser Trp Gly
            100                 105                 110

Gln Gly Thr Leu Val Thr Val Ser Ser
```

```
        115                 120


<210> SEQ ID NO 6
<211> LENGTH: 110
<212> TYPE: PRT
<213> ORGANISM: Artificial Sequence
<220> FEATURE:
<223> OTHER INFORMATION: L Variable region VH5

<400> SEQUENCE: 6

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

Asp Val Ser Trp Tyr Gln Gln Leu Pro Gly Thr Ala Pro Lys Leu Leu
        35                  40                  45

Ile Tyr Ala Asn Val Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Asp Ser Leu
                85                  90                  95

Asn Ala Tyr Val Phe Gly Cys Gly Thr Lys Leu Thr Val Leu
            100                 105                 110


<210> SEQ ID NO 7
<211> LENGTH: 121
<212> TYPE: PRT
<213> ORGANISM: Artificial Sequence
<220> FEATURE:
<223> OTHER INFORMATION: H Variable region VH16

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Cys Leu Glu Trp Val
        35                  40                  45

Ser Ala Ile Ser Gly Ser Asn Ala Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Val Leu Thr Thr Leu Met Asn Trp Phe Asp Tyr Trp Gly
            100                 105                 110

Gln Gly Thr Leu Val Thr Val Ser Ser
        115                 120


<210> SEQ ID NO 8
<211> LENGTH: 110
<212> TYPE: PRT
<213> ORGANISM: Artificial Sequence
<220> FEATURE:
<223> OTHER INFORMATION: L Variable region VH16

<400> SEQUENCE: 8

Gln Ser Val Leu Thr Gln Pro Pro Ser Ala Ser Gly Thr Pro Gly Gln
1               5                   10                  15
```

```
Arg Val Thr Ile Ser Cys Thr Gly Ser Ser Ser Asn Ile Gly Ser Asn
            20                  25                  30

Asp Val Ser Trp Tyr Gln Gln Leu Pro Gly Thr Ala Pro Lys Leu Leu
        35                  40                  45

Ile Tyr Ala Asn Val Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Asp Ser Leu
                85                  90                  95

Asn Ala Tyr Val Phe Gly Cys Gly Thr Lys Leu Thr Val Leu
            100                 105                 110


<210> SEQ ID NO 9
<211> LENGTH: 121
<212> TYPE: PRT
<213> ORGANISM: Artificial Sequence
<220> FEATURE:
<223> OTHER INFORMATION: H Variable region VH9

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Cys Leu Glu Trp Val
        35                  40                  45

Ser Ala Ile Ser Gly Asp Asn Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Val Leu Thr Thr Leu Met Asn Trp Phe Asp Ser Trp Gly
            100                 105                 110

Gln Gly Thr Leu Val Thr Val Ser Ser
        115                 120


<210> SEQ ID NO 10
<211> LENGTH: 110
<212> TYPE: PRT
<213> ORGANISM: Artificial Sequence
<220> FEATURE:
<223> OTHER INFORMATION: L Variable region VH9

<400> SEQUENCE: 10

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

Asp Val Ser Trp Tyr Gln Gln Leu Pro Gly Thr Ala Pro Lys Leu Leu
        35                  40                  45

Ile Tyr Ala Asn Ser Asn Arg Pro Ser Gly Val Ser Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Asp Ser Leu
```

```
                85                  90                  95

Asn Gly Tyr Val Phe Gly Cys Gly Thr Lys Leu Thr Val Leu
            100                 105                 110


<210> SEQ ID NO 11
<211> LENGTH: 251
<212> TYPE: PRT
<213> ORGANISM: Artificial Sequence
<220> FEATURE:
<223> OTHER INFORMATION: scFv 3_4

<400> SEQUENCE: 11

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

Asp Val Ser Trp Tyr Gln Gln Leu Pro Gly Thr Ala Pro Lys Leu Leu
        35                  40                  45

Ile Tyr Ala Asn Val Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Ala Gly Ser Leu
                85                  90                  95

Asn Ala Tyr Val Phe Gly Cys Gly Thr Lys Leu Thr Val Leu Gly Gly
            100                 105                 110

Gly Gly Ser Gly Gly Gly Gly Ser Gly Gly Gly Gly Ser Gly Gly Gly
        115                 120                 125

Gly Ser Glu Val Gln Leu Leu Glu Ser Gly Gly Gly Leu Val Gln Pro
    130                 135                 140

Gly Gly Ser Leu Arg Leu Ser Cys Ala Ala Ser Gly Phe Thr Phe Ser
145                 150                 155                 160

Ser Tyr Asp Met Ser Trp Val Arg Gln Ala Pro Gly Lys Cys Leu Glu
                165                 170                 175

Trp Val Ser Ala Ile Ser Tyr Asp Asn Ala Asn Thr Tyr Tyr Ala Asp
            180                 185                 190

Ser Val Lys Gly Arg Phe Thr Ile Ser Arg Asp Asn Ser Lys Asn Thr
        195                 200                 205

Leu Tyr Leu Gln Met Asn Ser Leu Arg Ala Glu Asp Thr Ala Val Tyr
    210                 215                 220

Tyr Cys Ala Lys Gly Val Leu Thr Thr Leu Met Asn Trp Phe Asp Tyr
225                 230                 235                 240

Trp Gly Gln Gly Thr Leu Val Thr Val Ser Ser
                245                 250


<210> SEQ ID NO 12
<211> LENGTH: 716
<212> TYPE: PRT
<213> ORGANISM: Artificial Sequence
<220> FEATURE:
<223> OTHER INFORMATION: hu11F11(ver.2)(M428L)-F06(de2)(StoP)

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Asp Phe
            20                  25                  30
```

```
Tyr Met Glu Trp Val Arg Gln Pro Pro Gly Lys Arg Leu Glu Trp Ile
        35                  40                  45

Ala Ala Ser Arg Asn Lys Ala Asn Asp Tyr Thr Thr Glu Tyr Ser Ala
    50                  55                  60

Ser Val Lys Gly Arg Phe Thr Val Ser Arg Asp Asp Ser Lys Ser Ser
65                  70                  75                  80

Leu Tyr Leu Gln Met Asn Ser Leu Arg Ala Glu Asp Thr Ala Ile Tyr
                85                  90                  95

Tyr Cys Ala Arg Asp Ala His Gly Lys Pro Phe Ala Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Leu His
            420                 425                 430

Glu Ala Leu His Asn His Tyr Thr Gln Lys Ser Leu Ser Leu Ser Pro
        435                 440                 445

Gly Lys Gly Gly Gly Gly Ser Gly Gly Gly Gly Ser Gly Gly Gly Gly
```

```
    450                 455                 460

Ser Gln Ser Val Leu Thr Gln Pro Pro Ser Ala Ser Gly Thr Pro Gly
465                 470                 475                 480

Gln Arg Val Thr Ile Ser Cys Thr Gly Ser Ser Ser Asn Ile Gly Ser
                485                 490                 495

Asn Asp Val Ser Trp Tyr Gln Gln Leu Pro Gly Thr Ala Pro Lys Leu
            500                 505                 510

Leu Ile Tyr Ala Asn Val Asn Arg Pro Ser Gly Val Pro Asp Arg Phe
        515                 520                 525

Ser Gly Ser Lys Ser Gly Thr Ser Ala Ser Leu Ala Ile Ser Gly Leu
    530                 535                 540

Arg Ser Glu Asp Glu Ala Asp Tyr Tyr Cys Gly Thr Trp Ala Gly Ser
545                 550                 555                 560

Leu Asn Ala Tyr Val Phe Gly Cys Gly Thr Lys Leu Thr Val Leu Gly
                565                 570                 575

Gly Gly Gly Ser Gly Gly Gly Gly Ser Gly Gly Gly Gly Ser Gly Gly
            580                 585                 590

Gly Gly Ser Glu Val Gln Leu Leu Glu Ser Gly Gly Gly Leu Val Gln
        595                 600                 605

Pro Gly Gly Ser Leu Arg Leu Ser Cys Ala Ala Ser Gly Phe Thr Phe
    610                 615                 620

Ser Ser Tyr Asp Met Ser Trp Val Arg Gln Ala Pro Gly Lys Cys Leu
625                 630                 635                 640

Glu Trp Val Ser Ala Ile Ser Tyr Asp Asn Ala Asn Thr Tyr Tyr Ala
                645                 650                 655

Asp Ser Val Lys Gly Arg Phe Thr Ile Ser Arg Asp Asn Ser Lys Asn
            660                 665                 670

Thr Leu Tyr Leu Gln Met Asn Ser Leu Arg Ala Glu Asp Thr Ala Val
        675                 680                 685

Tyr Tyr Cys Ala Lys Gly Val Leu Thr Thr Leu Met Asn Trp Phe Asp
    690                 695                 700

Tyr Trp Gly Gln Gly Thr Leu Val Thr Val Ser Ser
705                 710                 715


<210> SEQ ID NO 13
<211> LENGTH: 450
<212> TYPE: PRT
<213> ORGANISM: Artificial Sequence
<220> FEATURE:
<223> OTHER INFORMATION: hu11F11(ver.2)(M428L)

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Asp Phe
            20                  25                  30

Tyr Met Glu Trp Val Arg Gln Pro Pro Gly Lys Arg Leu Glu Trp Ile
        35                  40                  45

Ala Ala Ser Arg Asn Lys Ala Asn Asp Tyr Thr Thr Glu Tyr Ser Ala
    50                  55                  60

Ser Val Lys Gly Arg Phe Thr Val Ser Arg Asp Asp Ser Lys Ser Ser
65                  70                  75                  80

Leu Tyr Leu Gln Met Asn Ser Leu Arg Ala Glu Asp Thr Ala Ile Tyr
                85                  90                  95

Tyr Cys Ala Arg Asp Ala His Gly Lys Pro Phe Ala Tyr Trp Gly Gln
```

-continued

```
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Leu His
            420                 425                 430

Glu Ala Leu His Asn His Tyr Thr Gln Lys Ser Leu Ser Leu Ser Pro
        435                 440                 445

Gly Lys
    450


<210> SEQ ID NO 14
<211> LENGTH: 15
<212> TYPE: PRT
<213> ORGANISM: Artificial Sequence
<220> FEATURE:
<223> OTHER INFORMATION: (G4S)3

<400> SEQUENCE: 14

Gly Gly Gly Gly Ser Gly Gly Gly Gly Ser Gly Gly Gly Gly Ser
```

-continued 1 5 10 15

<210> SEQ ID NO 15
<211> LENGTH: 110
<212> TYPE: PRT
<213> ORGANISM: Artificial Sequence
<220> FEATURE:
<223> OTHER INFORMATION: F06(de2)(StoP) VL

<400> SEQUENCE: 15

Gln Ser Val Leu Thr Gln Pro Pro Ser Ala Ser Gly Thr Pro Gly Gln
1 5 10 15

Arg Val Thr Ile Ser Cys Thr Gly Ser Ser Ser Asn Ile Gly Ser Asn
20 25 30

Asp Val Ser Trp Tyr Gln Gln Leu Pro Gly Thr Ala Pro Lys Leu Leu
35 40 45

Ile Tyr Ala Asn Val Asn Arg Pro Ser Gly Val Pro Asp Arg Phe Ser
50 55 60

Gly Ser Lys Ser Gly Thr Ser Ala Ser Leu Ala Ile Ser Gly Leu Arg
65 70 75 80

Ser Glu Asp Glu Ala Asp Tyr Tyr Cys Gly Thr Trp Ala Gly Ser Leu
85 90 95

Asn Ala Tyr Val Phe Gly Cys Gly Thr Lys Leu Thr Val Leu
100 105 110

<210> SEQ ID NO 16
<211> LENGTH: 20
<212> TYPE: PRT
<213> ORGANISM: Artificial Sequence
<220> FEATURE:
<223> OTHER INFORMATION: (G4S)4

<400> SEQUENCE: 16

Gly Gly Gly Gly Ser Gly Gly Gly Gly Ser Gly Gly Gly Gly Ser Gly
1 5 10 15

Gly Gly Gly Ser
20

<210> SEQ ID NO 17
<211> LENGTH: 121
<212> TYPE: PRT
<213> ORGANISM: Artificial Sequence
<220> FEATURE:
<223> OTHER INFORMATION: F06(de2)(StoP) VH

<400> SEQUENCE: 17

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Asp Met Ser Trp Val Arg Gln Ala Pro Gly Lys Cys Leu Glu Trp Val
35 40 45

Ser Ala Ile Ser Tyr Asp Asn Ala Asn Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gly Val Leu Thr Thr Leu Met Asn Trp Phe Asp Tyr Trp Gly
100 105 110

```
Gln Gly Thr Leu Val Thr Val Ser Ser
        115                 120


<210> SEQ ID NO 18
<211> LENGTH: 115
<212> TYPE: PRT
<213> ORGANISM: Artificial Sequence
<220> FEATURE:
<223> OTHER INFORMATION: ch1E4 VH

<400> SEQUENCE: 18

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Val Lys Gln Arg Pro Gly Gln Gly Leu Glu Trp Ile
        35                  40                  45

Gly Val Ile Asn Pro Gly Ser Gly Gly Thr Asn Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Asp Asp Ser Ala Val Tyr Phe Cys
                85                  90                  95

Ala Ser Gly Asn Tyr Asp Thr Tyr Trp Gly Gln Gly Thr Leu Val Thr
            100                 105                 110

Val Ser Ala
        115


<210> SEQ ID NO 19
<211> LENGTH: 112
<212> TYPE: PRT
<213> ORGANISM: Artificial Sequence
<220> FEATURE:
<223> OTHER INFORMATION: ch1E4 VL

<400> SEQUENCE: 19

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Arg Thr Phe Gly Gly Gly Thr Lys Leu Glu Ile Lys
            100                 105                 110


<210> SEQ ID NO 20
<211> LENGTH: 2148
<212> TYPE: DNA
<213> ORGANISM: Artificial Sequence
<220> FEATURE:
<223> OTHER INFORMATION: hu11F11 F06 monovalent conatant vector 1

<400> SEQUENCE: 20
```

-continued

```
gaggtgcagc tcgtagagtc aggcggggga ctcgtccaac ccggtggttc tcttagattg     60
tcatgtgcca caagcggttt taccttttcc gatttttaca tggagtgggt tcgtcagcca    120
ccagggaagc gacttgagtg gatcgcagca tcccgtaata aggccaatga ctatactacc    180
gagtattccg cttcagtaaa gggcagattc accgtcagta gggatgacag caagagcagc    240
ctctatctcc agatgaatag tctgagggct gaagataccg ccatttacta ctgtgcacgg    300
gatgctcatg ggaagccctt cgcttactgg ggccaaggca ccactgtaac cgtatcctct    360
gcctccacca agggcccctc cgtgttcccc ctggcccccct cctccaagtc cacctccggc   420
ggcaccgccg ccctgggctg cctggtgaag gactacttcc ccgagcccgt gaccgtgtcc    480
tggaactccg gcgccctgac ctccggcgtg cacaccttcc ccgccgtgct gcagtcctcc    540
ggcctgtact ccctgtcctc cgtcgtgacc gtgccctcct cctccctggg cacccagacc    600
tacatctgca acgtgaacca caagccctcc aacaccaagg tggacaagaa ggtggagccc    660
aagtcctgcg acaagaccca cacctgccct ccctgccccg cccccgagct gctgggcggc    720
ccctccgtgt tcctgttccc tcctaagccc aaggacaccc tgatgatctc ccggaccccc    780
gaggtgactt gcgtggtggt ggacgtgtcc cacgaggacc ccgaggtgaa gttcaactgg    840
tacgtggacg gcgtggaggt gcacaacgcc aagaccaagc cccgggagga gcagtacaac    900
tccacctacc gggtggtgtc cgtgctgacc gtgctgcacc aggactggct gaacggcaag    960
gagtacaagt gcaaggtgtc caacaaggcc ctgcccgccc ccatcgagaa gaccatctcc   1020
aaggccaagg gccagccccg ggagccccag gtgtacaccc tgccccccctc ccgggatgaa  1080
cttactaaga accaggtctc tctgtcatgc gccgtcaaag gtttttatcc atccgacatt   1140
gccgtcgagt gggagtcaaa tggtcagcca gagaataact acaagacaac tccacccgtg   1200
ctcgactccg acggcagctt ctttttggtg tccaagttga ccgttgacaa gtctcgttgg   1260
caacagggta acgtattttc ctgtagtgtc cttcacgagg ccctgcataa ccactatact   1320
caaaaatctc tgtccctgag ccctggaaaa ggtggcggag gatctggcgg tggtggttct   1380
ggcggaggcg gatctcagtc tgttctgacc cagcctcctt ctgcttctgg cacccctggc   1440
cagagagtga ccatctcttg taccggctcc tcctccaaca tcggctccaa cgacgtgtcc   1500
tggtatcagc agctgcctgg cacagcccct aaactgctga tctacgccaa cgtaaaccgg   1560
ccttctggcg tgcctgacag attctccggc tccaagtctg gcacctctgc ctccctggct   1620
atctccggcc tgagatctga ggacgaggcc gattactact gcggcacctg ggccggatct   1680
ctgaacgcct atgtgttcgg ctgcggcaca aagctgacag tgttgggagg cggaggaagt   1740
ggtggcggcg gttcaggcgg cggtggcagc ggaggtggtg gatctgaagt tcagctgctg   1800
gaatctggcg gcggattggt tcagcctggt ggctctctga gactgtcttg tgccgcctct   1860
ggcttcacct tctccagcta cgatatgtcc tgggtccgac aggcccctgg caagtgtttg   1920
gagtgggtgt ccgccatctc ctacgacaac gccaacacct actacgccga ctccgtgaag   1980
ggccggttca ccatctctcg ggacaacagc aagaacaccc tgtacctgca gatgaactcc   2040
ctgagagccg aggacaccgc cgtgtactat tgtgctaagg gcgtgctgac caccctgatg   2100
aattggttcg attactgggg ccagggcacc ctggtcaccg tgtcatct                2148
```

<210> SEQ ID NO 21
<211> LENGTH: 1350
<212> TYPE: DNA
<213> ORGANISM: Artificial Sequence
<220> FEATURE:
<223> OTHER INFORMATION: hu11F11 F06 monovalent conatant vector 2

<400> SEQUENCE: 21
gaggtgcagc tcgtagagtc aggcgggggga ctcgtccaac ccggtggttc tcttagattg 60
tcatgtgcca caagcggttt taccttttcc gatttttaca tggagtgggt tcgtcagcca 120
ccagggaagc gacttgagtg gatcgcagca tcccgtaata aggccaatga ctatactacc 180
gagtattccg cttcagtaaa gggcagattc accgtcagta gggatgacag caagagcagc 240
ctctatctcc agatgaatag tctgagggct gaagataccg ccatttacta ctgtgcacgg 300
gatgctcatg ggaagccctt cgcttactgg ggccaaggca ccactgtaac cgtatcctct 360
gcctccacca agggcccctc cgtgttcccc ctggccccct cctccaagtc cacctccggc 420
ggcaccgccg ccctgggctg cctggtgaag gactacttcc ccgagcccgt gaccgtgtcc 480
tggaactccg gcgccctgac ctccggcgtg cacaccttcc ccgccgtgct gcagtcctcc 540
ggcctgtact ccctgtcctc cgtcgtgacc gtgccctcct cctccctggg cacccagacc 600
tacatctgca acgtgaacca caagccctcc aacaccaagg tggacaagaa ggtggagccc 660
aagtcctgcg acaagaccca cacctgccct ccctgccccg cccccgagct gctgggcggc 720
ccctccgtgt tcctgttccc tcctaagccc aaggacaccc tgatgatctc ccggaccccc 780
gaggtgactt gcgtggtggt ggacgtgtcc cacgaggacc ccgaggtgaa gttcaactgg 840
tacgtggacg gcgtggaggt gcacaacgcc aagaccaagc cccgggagga gcagtacaac 900
tccacctacc gggtggtgtc cgtgctgacc gtgctgcacc aggactggct gaacggcaag 960
gagtacaagt gcaaggtgtc caacaaggcc ctgcccgccc ccatcgagaa gaccatctcc 1020
aaggccaagg gccagccccg ggagccccag gtgtacaccc tgcccccctc ccgtgatgaa 1080
ctcactaaga atcaagtcag tctctggtgt ttggtcaaag gcttctatcc atctgatatt 1140
gctgttgaat gggagagtaa cggcaacct gaaaataatt acaagactac acctcccgtg 1200
cttgattccg acggttcctt ctttctgtat tccaagctga cagttgataa gagtcgctgg 1260
cagcagggga acgtatttag ttgttctgta cttcacgaag ctctccataa ccattacact 1320
caaaagtccc tgtccctgtc ccccggcaag 1350

<210> SEQ ID NO 22
<211> LENGTH: 660
<212> TYPE: DNA
<213> ORGANISM: Artificial Sequence
<220> FEATURE:
<223> OTHER INFORMATION: hu11F11 F06 monovalent variable vector

<400> SEQUENCE: 22
gatatcgtga tgacccagtc tccttcctct ctggctgtgt ccctgggcga gcgcgtcacc 60
atgtcctgca agtcctctca gtccctgctg tactcctcca accagaagaa ctacctggcc 120
tggtatcagc agaagcccgg ccagtctcca aagctgctga tctactgggc ctccaccaga 180
gaatctggcg tgccagatag attcaccggc tctggctctg gcaccgactt caccctgaca 240
atctcttccg tgaaggccga ggacgtggcc gtgtactact gccagcagta ctacagctac 300
ccctggacct ttggcggagg caccaagctg gaaatcaagc ggaccgtggc cgctccctcc 360
gtgttcatct tcccaccctc cgacgagcag ctgaagtccg gcaccgcttc cgtcgtgtgc 420
ctgctgaaca acttctaccc ccgcgaggcc aaggtgcagt ggaaggtgga caacgccctg 480
cagtccggca actcccagga atccgtcacc gagcaggact ccaaggacag cacctacagc 540
ctgtcctcca ccctgaccct gtccaaggcc gactacgaga agcacaaggt gtacgcctgc 600
gaagtgaccc accagggcct gtccagcccc gtgaccaagt ccttcaaccg gggcgagtgc 660

<210> SEQ ID NO 23
<211> LENGTH: 8
<212> TYPE: PRT
<213> ORGANISM: Artificial Sequence
<220> FEATURE:
<223> OTHER INFORMATION: human VH3 domain sequence

<400> SEQUENCE: 23

Leu Tyr Leu Gln Met Asn Ser Leu
1 5

<210> SEQ ID NO 24
<211> LENGTH: 8
<212> TYPE: PRT
<213> ORGANISM: Artificial Sequence
<220> FEATURE:
<223> OTHER INFORMATION: human VH3 domain sequence

<400> SEQUENCE: 24

Asn Tyr Leu Gln Met Asn Ser Leu
1 5

<210> SEQ ID NO 25
<211> LENGTH: 8
<212> TYPE: PRT
<213> ORGANISM: Artificial Sequence
<220> FEATURE:
<223> OTHER INFORMATION: human VH3 domain sequence

<400> SEQUENCE: 25

Leu His Leu Gln Met Asn Ser Leu
1 5

<210> SEQ ID NO 26
<211> LENGTH: 8
<212> TYPE: PRT
<213> ORGANISM: Artificial Sequence
<220> FEATURE:
<223> OTHER INFORMATION: human VH3 domain sequence

<400> SEQUENCE: 26

Leu Tyr Leu Gln Met Asp Ser Leu
1 5

<210> SEQ ID NO 27
<211> LENGTH: 8
<212> TYPE: PRT
<213> ORGANISM: Artificial Sequence
<220> FEATURE:
<223> OTHER INFORMATION: human VH3 domain sequence

<400> SEQUENCE: 27

Ala Tyr Leu Gln Met Asn Ser Leu
1 5

<210> SEQ ID NO 28
<211> LENGTH: 8
<212> TYPE: PRT
<213> ORGANISM: Artificial Sequence
<220> FEATURE:
<223> OTHER INFORMATION: human VH3 domain sequence

<400> SEQUENCE: 28

Thr Tyr Leu Gln Met Asn Ser Leu
1 5

<210> SEQ ID NO 29
<211> LENGTH: 8
<212> TYPE: PRT
<213> ORGANISM: Artificial Sequence
<220> FEATURE:
<223> OTHER INFORMATION: human VH3 domain sequence

<400> SEQUENCE: 29

Met Tyr Leu Gln Met Ser Asn Leu
1 5

<210> SEQ ID NO 30
<211> LENGTH: 8
<212> TYPE: PRT
<213> ORGANISM: Artificial Sequence
<220> FEATURE:
<223> OTHER INFORMATION: human VH3 domain sequence

<400> SEQUENCE: 30

Leu Tyr Leu Gln Met Ser Ser Leu
1 5

<210> SEQ ID NO 31
<211> LENGTH: 8
<212> TYPE: PRT
<213> ORGANISM: Artificial Sequence
<220> FEATURE:
<223> OTHER INFORMATION: human VH3 domain sequence

<400> SEQUENCE: 31

Met Tyr Leu Gln Met Asn Asn Leu
1 5

<210> SEQ ID NO 32
<211> LENGTH: 8
<212> TYPE: PRT
<213> ORGANISM: Artificial Sequence
<220> FEATURE:
<223> OTHER INFORMATION: human VH3 domain sequence

<400> SEQUENCE: 32

Leu Tyr Leu Gln Val Asn Ser Leu
1 5

<210> SEQ ID NO 33
<211> LENGTH: 8
<212> TYPE: PRT
<213> ORGANISM: Artificial Sequence
<220> FEATURE:
<223> OTHER INFORMATION: human VH3 domain sequence

<400> SEQUENCE: 33

Leu Tyr Leu Gln Thr Asn Ser Leu
1 5

<210> SEQ ID NO 34
<211> LENGTH: 8
<212> TYPE: PRT
<213> ORGANISM: Artificial Sequence
<220> FEATURE:
<223> OTHER INFORMATION: human VH3 domain sequence

<400> SEQUENCE: 34

Leu Phe Leu Gln Met Asn Ser Leu
1 5

```
<210> SEQ ID NO 35
<211> LENGTH: 8
<212> TYPE: PRT
<213> ORGANISM: Artificial Sequence
<220> FEATURE:
<223> OTHER INFORMATION: human VH3 domain sequence

<400> SEQUENCE: 35

Leu Tyr Val Gln Met Ser Ser Leu
1               5


<210> SEQ ID NO 36
<211> LENGTH: 8
<212> TYPE: PRT
<213> ORGANISM: Artificial Sequence
<220> FEATURE:
<223> OTHER INFORMATION: human VH3 domain sequence

<400> SEQUENCE: 36

Leu Tyr Leu Gln Met Gly Ser Leu
1               5


<210> SEQ ID NO 37
<211> LENGTH: 8
<212> TYPE: PRT
<213> ORGANISM: Artificial Sequence
<220> FEATURE:
<223> OTHER INFORMATION: human VH3 domain sequence

<400> SEQUENCE: 37

Met Tyr Leu Gln Met Asn Ser Leu
1               5
```

METHOD FOR PURIFYING BIOLOGICALLY ACTIVE PEPTIDE BY USING PROTEIN A AFFINITY CHROMATOGRAPHY

SEQUENCE LISTING SUBMISSION VIA EFS-WEB

A computer readable text file, entitled "SequenceListing.txt," created on Jun. 10, 2022 Jul. 7, 2022 with a file size of 37,396 bytes contains the sequence listing for this application and is hereby incorporated by reference in its entirety.

TECHNICAL FIELD

The present disclosure relates to a method of purifying an Fc-containing bioactive peptide using protein A affinity chromatography, and more particularly, a method of purifying a specific peptide with high purity from a peptide mixture by using the difference in binding affinity to protein A according to the difference in the number of human VH3 domains included in a Fc-containing bioactive peptide.

BACKGROUND ART

Various purification methods are used to isolate specific peptides. For example, ion exchange chromatography, hydrophobic chromatography, size exclusion chromatography, affinity chromatography, and the like are used.

However, in the case of peptides having similar structures, the differences thereof in the isoelectric point, hydrophobicity, size, and affinity are small. Accordingly, purification methods of the related art are not suitable for obtaining a specific peptide with high purity. In this regard, there are many known purification methods of artificially changing the sequence to cause the difference in an isoelectric point and affinity between a specific target peptide and other peptides that can be generated. In both cases, due to the artificial sequence changes to increase the difference in the isoelectric point or affinity, physicochemical properties of specific peptides are changed, and unpredictable immunogenicity may be induced therefrom.

DESCRIPTION OF EMBODIMENTS

Technical Problem

The present disclosure provides a method of purifying, from a peptide mixture or an antibody mixture, a Fc-containing bioactive peptide or antibody to a high level of purity through affinity chromatography, using the difference in the binding affinity to protein A caused by the difference in the number of human VH3 domains of the Fc-containing bioactive peptides contained in a bioactive peptide mixture. The present disclosure provides a method of providing a target peptide having high purity by separating peptides having different numbers of VH3 domains according to the number of VH3 domains through affinity chromatography using the difference in affinity with the full domain protein A thereof, in the case where peptides that have similar affinity or isoelectric properties and different numbers of VH3 domains are prepared, wherein the affinity with the full domain protein A depends on the number of VH3 domains included in a peptide.

In particular, the present disclosure provides a method of separating and purifying an asymmetric heterodimeric protein and a homodimeric protein based on the difference in the number of VH3 domains included in a protein in the case where unwanted homodimer proteins are generated during the production of an asymmetric heterodimer protein.

Solution to Problem

Each description and embodiment described herein is applicable to other descriptions and other embodiment. That is, all combinations of the various components described herein fall within the scope of the present disclosure.

In addition, it would not be constructed that the following descriptions do not limit the scope of the present disclosure.

Terms such as first, second, etc. used herein may be used to describe various components, but the components should not be limited by the terms. The above terms are used only for the purpose of distinguishing one component from another. For example, without departing from the scope of the present disclosure, a first component may be referred to as a second component, and similarly, a second component may also be referred to as a first component. The singular expression includes the plural expression unless the context clearly dictates otherwise.

Unless defined otherwise, all terms (including technical and scientific terms) used herein have the same meaning as commonly understood by one of ordinary skill in the art to which this disclosure belongs. Also, terms such as those defined in commonly used dictionaries should be construed as having a meaning consistent with their meaning in the context of the relevant art, and unless interpreted in an ideal or overly formal sense, they are understood as the same as explicitly defined herein.

Terms such as "including" or "containing" are intended to designate the presence of a feature, a number, a step, an action, a component, or a combination thereof described in the specification, and should be understood that the presence or possibility of addition of one or more other features, one or more other numbers, one or more other steps, one or more other actions, one or more other components, or one or more there combinations thereof are not excluded.

"and/or" includes any combination of one or more that the associated configurations may define.

The term "bioactive peptide" used herein includes peptides, polypeptides, proteins, parts of proteins, fusion proteins, etc., each of which exhibits one or more physiological activities, and is not limited by a specific molecular weight or the length, type, etc. of amino acids.

The term "Fc-containing bioactive peptide" used herein refers to a bioactive peptide including a fragment crystallizable region (an Fc region) found in an antibody. For example, the Fc-containing bioactive peptide is a material including an antibody containing an Fc region.

The present disclosure may provide a method of separating and/or purifying Fc-containing bioactive peptides from a mixture of Fc-containing bioactive peptides.

The bioactive peptide used herein refers to a peptide that is delivered to an organism and modulates the function of the organism, and peptides that control biological functions, such as hormones, cytokines, enzymes, antibodies, growth factors, transcriptional regulators, blood factors, vaccines, structural proteins, ligand proteins, or receptors, may be defined as bioactive materials. For example, these peptides may be in the form of being connected to the N-terminus or C-terminus of Fc.

An embodiment of the present disclosure provides a method of purifying a Fc-containing bioactive peptide including: (a) loading a mixture of Fc-containing bioactive peptides into a column including an affinity matrix containing protein A ligand, wherein the mixture of bioactive peptides includes a first Fc-containing bioactive peptide and a second Fc-containing bioactive peptide, and the second Fc-containing bioactive peptide includes at least one more human VH3 domain, compared to the first Fc-containing bioactive peptide; and (b) loading an eluate into the column to separate and elute the Fc-containing bioactive peptides at different pH depending on the number of human VH3 domains included in each of the Fc-containing bioactive peptides included in the mixture of bioactive peptides.

In an embodiment, the second Fc-containing bioactive peptide may include at least one more human VH3 domain, compared to the first Fc-containing bioactive peptide, or at least one more amino acid sequence having 95% or more, 90% or more, 80% or more, or 70% or more homology with the human VH3 domain, compared to the first Fc-containing bioactive peptide. The human VH3 domain is an amino acid sequence located between the CDR2 and CDR3 of the heavy chain variable region of a VH3-family human antibody, and may include any one of SEQ ID No. 23 to SEQ ID No. 37, but is not limited thereto, and a person skilled in the art may easily determine the sequence of the human VH3 domain contained in a protein. The human VH3 domain is mainly present in a VH3-family human antibody, but is rarely found in the framework of mammalian (or chimeric) antibodies such as mouse. For example, hu11F11 used in the Examples of the present disclosure is an antibody containing a human VH3 domain, and ch1E4 and anti-BACE antibodies are antibodies that do not include a human VH3 domain. Exceptionally, ch11F11 is an antibody including a human VH3 domain even though ch11F11 is a chimeric antibody.

The protein A ligand may be a full domain protein A ligand. That is, the protein A ligand may include all of the full domains (E, D, A, B, and C domains). However, embodiments are not limited thereto, and the protein A ligand may include one or more domains selected from an E domain and a D domain. For example, the protein A ligand may include an E domain and a D domain.

A support for supporting the protein A ligand in the affinity matrix may be particles having a bead shape, such as a spherical shape. The average particle size of the support in the affinity matrix may be, for example, less than about 90 μm, for example, about 80 μm or less or 75 μm or less. In addition, the average particle size of the support in the affinity matrix may be, for example, about 1 μm or more or 5 μm or more. When the size of the support in the affinity matrix satisfies these ranges, the bioactive peptide may have excellent separation ability.

The process (b) may include: (b1) eluting the first Fc-containing bioactive peptide by loading an eluate having a first pH range into the column; and (b2) eluting the second Fc-containing bioactive peptide by loading an eluate having a second pH range lower than the first pH range into the column. The eluate having the first pH range and the eluate having the second pH range may be loaded into the column separately or sequentially, or the eluate may be continuously loaded into the column such that the concentration gradient occurs according to the loading time from the first pH range to the second pH range.

The mixture of bioactive peptides may further include a third Fc-containing bioactive peptide which includes at least one more human VH3 domain, compared to the second Fc-containing bioactive peptide.

According to the purification method of the present disclosure, the first Fc-containing bioactive peptide, the second Fc-containing bioactive peptide, and the third Fc-containing bioactive peptide, which have different numbers of VH3 domains, may be separated and purified, and each of these may be purified with high purity.

Moreover, the present disclosure does not exclude Fc as a component of a purification target material, and the binding between Fc and protein A is also considered in the purification process. Since Fc itself has affinity to protein A, it is common to exclude the affinity of components other than Fc in the purification method using affinity between Fc and protein A, and in the opposite case, it is common to exclude the affinity to Fc. Meanwhile, the present disclosure provides a method of purifying a Fc-containing bioactive peptide having both heavy chain Fc and a VH3 domain as components, according to the number of VH3 domains.

In relation to the mixture of bioactive peptides, the first Fc-containing bioactive peptide may include n human VH3 domains (n is an integer greater than or equal to 0), the second Fc-containing bioactive peptide may include n+1 to n+9 human VH3 domains, and the third Fc-containing bioactive peptide may include n+2 to n+10 human VH3 domains. In an embodiment, the first Fc-containing bioactive peptide may include n human VH3 domains (n is an integer greater than or equal to 0), the second Fc-containing bioactive peptide may include n+1 human VH3 domains, and the third Fc-containing bioactive peptide may include n+2 human VH3 domains.

n may be, for example, 0 or more and 10 or less, 0 or more and 8 or less, 0 or more 6 or less, 0 or more and 5 or less, 0 or more and 3 or less, 1 or more and 10 or less, 1 or more and 8 or less, 1 or more and 6 or less, 1 or more and 5 or less, 1 or more and 3 or less, 2 or more and 10 or less, 2 or more and 8 or less, 2 or more and 6 or less, 2 or more and 5 or less. n may be, for example, 0, 1, 2, or 3.

The process (b) includes: (b1) eluting the first Fc-containing bioactive peptide by loading the eluate having the first pH range into the column; (b2) eluting the second Fc-containing bioactive peptide by loading the eluate having the second pH range lower than the first pH range into the column; and (b3) eluting the third Fc-containing bioactive peptide by using an eluate having a third pH range lower than the second pH range. Herein, the steps (b1) to (b3) may be consecutively performed (linear gradient). That is, the steps (b1) to (b2) are performed such that each of the first to third pH ranges is not intermittent and are included in a continuous pH range between the start value of the first pH range and the end value of the third pH range, and initially, the eluate having the first pH range is loaded into the column, and continuously, the pH of the eluate loaded is gradually lowered so that the pH of the eluate is gradually to be within the second pH range and the third pH range. In addition, the pH range at which peptides are eluted may vary depending on the kind of the purification target bioactive peptide.

In an embodiment, the steps (b1) to (b2) may be performed in steps (step gradient).

The Fc may be an Fc to which a mutation affecting binding to wild-type protein A is not introduced. The mutation refers to a polypeptide in which insertion, deletion, addition, and/or substitution have occurred at one or more amino acid residues, compared to the polypeptide sequence of Fc. That is, in the Fc according to an embodiment, a mutation that inhibits the binding to protein A or a mutation that increases the binding to protein A may not be introduced.

The first, second, and/or third Fc-containing bioactive peptide may include a peptide drug bound to the Fc. Herein, the "peptide drug" refers to an independent peptide bound to the bioactive peptide while having a bio-activity that is the same as or different from that of the bioactive peptide.

In the Fc-containing bioactive peptides, the peptide drug may be bound to the N- or C-terminus of the Fc. For example, in the Fc-containing bioactive peptides, the peptide drug may be bound to one or more selected from two N-termini and two C-termini of the two heavy chains of the Fc.

The term "binding" used herein is defined as including a case where two objects are physically or chemically bound to each other directly, and a case where two objects are bound or connected to each other through a linker. In an embodiment, when Fc and a peptide drug are connected through a linker, the linker may be, for example, a peptide, and the linker may be any material that is used to connect a peptide in the art.

The peptide drug may be at least one selected from hormones, cytokines, enzymes, antibodies, growth factors, transcriptional regulators, blood factors, vaccines, structural proteins, ligand proteins, and receptors. For example, the peptide drug may include at least one selected from a human growth hormone, a growth hormone releasing hormone, a growth hormone releasing peptide, interferons, interferon receptors, colony stimulating factors, glucacon-like peptides such as GLP-1, a G-protein-coupled receptor, interleukins, interleukin receptors, enzymes, interleukin-binding protein, cytokine-binding protein, a macrophage activator, a macrophage peptide, a B cell factor, a T cell factor, an allergy suppressing factor, a cell necrosis glycoprotein, immunotoxin, lymphotoxin, a tumor necrosis factor, a tumor suppressing factor, a metastatic growth factor, alpha-1 antitrypsin, albumin, α-lactalbumin, apolipoprotein-E, erythropoietin, hyperglycosylated erythropoietin, angiopoeitins, hemoglobin, chrombin, a thrombin receptor activating peptide, thrombomodulin, blood factors VII, VIIa, VIII, IX, and XIII, plasminogen activator, fibrin-binding peptide, urokinase, strepto kinase, hirudin, protein C, C-reactive protein, renin inhibitor, collagenase inhibitor, superoxide dismutase, leptin, a platelet-derived growth factor, an epithelial growth factor, an epidermal growth factor, angiostatin, angiotensin, an osteogenic growth factor, an osteogenic promoting protein, calcitonin, insulin, atriopeptin, a cartilage inducer, elcatonin, a connective tissue activator, a tissue factor pathway inhibitor, a follicle stimulating hormone, a luteinizing hormone, a luteinizing hormone releasing hormone, nerve growth factors, a parathyroid hormone, relaxin, secretin, somatomedin, an insulin-like growth factor, an adrenal cortical hormone, glucagon, cholecystokinin, a pancreatic polypeptide, a gastrin releasing peptide, a corticotropin releasing factor, a thyroid stimulating hormone, autotaxin, lactoferrin, myostatin, receptors, a receptor antagonist, a cell surface antigen, a virus-derived vaccine antigen, a monoclonal antibody, a polyclonal antibody, and antibody fragments.

The glucagon-like peptide may include at least one selected from exenatide, liraglutide, taspoglutide, albiglutide, lixisenatide, and GLP-1, and may be, for example, GLP-1.

When the first or second Fc-containing bioactive peptide includes a VH3 domain, the first and second Fc-containing bioactive peptides may each independently be a VH domain-containing variable region sequence of any one of: the heavy chain variable region sequence of SEQ ID No. 1 and the light chain variable region sequence of SEQ ID No. 2; the heavy chain variable region sequence of SEQ ID No. 3 and the light chain variable region sequence of SEQ ID No. 4; the heavy chain variable region sequence of SEQ ID No. 5 and the light chain variable region sequence of SEQ ID No. 6; the heavy chain variable region sequence of SEQ ID No. 7 and the light chain variable region sequence of SEQ ID No. 8; or the heavy chain variable region sequence of SEQ ID No. 9 and the light chain variable region sequence of SEQ ID No. 10, and, for example, the heavy chain variable region sequence and the light chain variable region sequence may be a heavy chain variable region sequence and a light chain variable region sequence of an scFv.

The third Fc-containing bioactive peptide may include a VH domain-containing variable region sequence of any one of: the heavy chain variable region sequence of SEQ ID No. 1 and the light chain variable region sequence of SEQ ID No. 2; the heavy chain variable region sequence of SEQ ID No.3 and the light chain variable region sequence of SEQ ID No.4; the heavy chain variable region sequence of SEQ ID No. 5 and the light chain variable region sequence of SEQ ID No. 6; the heavy chain variable region sequence of SEQ ID No. 7 and the light chain variable region sequence of SEQ ID No. 8; or the heavy chain variable region sequence of SEQ ID No. 9 and the light chain variable region sequence of SEQ ID No. 10, and for example, the heavy chain variable region sequence and the light chain variable region sequence may be a heavy chain variable region sequence and a light chain variable region sequence of an scFv.

However, since the VH3 domain is included in the heavy chain variable region sequence, an scFv consisting of the heavy chain variable region sequence selected from these sequences and other light chain variable region sequences, or a single-chain antibody consisting of only a heavy chain variable region sequence selected from these sequences may also be included in the Fc-containing bioactive peptide.

The Fc-containing bioactive peptide may be an antibody containing immunoglobulin G (hereinafter, IgG).

The term "antibody" as used herein may refer to an intact immunoglobulin of any isotype, an antigen-binding fragment capable of competing with a complete antibody to bind to a target antigen, or a combination thereof. For example, the antibody may include a mouse antibody, a chimeric antibody, a humanized antibody, a complete human antibody, an antigen-binding fragment thereof, or a combination thereof. The antibody may itself be a type of antigen binding protein. An antibody generally includes at least two full-length heavy chains and two full-length light chains, although in some cases, the antibody includes heavy chains alone. The antibody may include a monospecific antibody that specifically binds to one target, and a multispecific antibody (for example, a bispecific antibody and a trispecific antibody) that specifically binds to a plurality of targets.

The antibody also includes a monoclonal antibody and a polyclonal antibody, and the monoclonal antibody may be an isolated antibody that specifically binds to IGF1R, which is a human antibody, a humanized antibody, or a chimeric antibody. The monoclonal antibody may be an isolated antibody that specifically binds to IGF1R, which is of type IgG1, IgG2, IgG3, or IgG4.

The term "light chain" as used herein may include a full-length light chain and fragments thereof, having a variable region sequence sufficient to provide binding specificity to an antigen or epitope. The full-length light chain may include a variable region domain VL, and a constant region domain CL. The variable region domain of the light chain may be at the amino terminus of the light chain polypeptide. Types of light chains may include kappa and lambda chains.

The term "complementarity-determining region (CDR)" as used herein may refer to a portion of the antibody variable region which provides a binding specificity to an antigen.

The term "heavy chain" as used herein may include a full-length heavy chain and fragments thereof, having a variable region sequence sufficient to provide a binding specificity to an antigen or epitope. A full-length heavy chain may include a variable region domain and three constant region domains CH1, CH2 and CH3. The variable region (VH) domain is at the amino terminus of the heavy chain polypeptide, the constant region (CH) domain is at the carboxy terminus, and CH3 may be located closest to the carboxy-terminus. The heavy chain may include isotypes of IgG (including IgG1, IgG2, IgG3, and IgG4 subtypes), IgA (including IgA1 and IgA2 subtypes), IgM, and IgE.

The antibody may be selected from all subtypes of immunoglobulins (for example, IgA, IgD, IgE, IgG (IgG1, IgG2, IgG3, IgG4), and IgM). The IgG type of antibody may be in the subtype of IgG1, IgG2, IgG3, or IgG4, for example, IgG1 or IgG2. The IgG-type antibody includes two heavy chains and two light chains, and the heavy chains and the light chains are bound through a disulfide bond to form two heavy chain-light chain structures (dimers), and the formed two dimers may be connected through a disulfide bond in the Fc region of the heavy chain. The IgG-type antibody may be a single target antibody targeting one antigen by including an antigen-binding site for the same antigen in both heavy chain-light chain constructs, or a bispecific antibody targeting two antigens by including antigen-binding sites for different antigens in both heavy chain-light chain constructs.

Antibodies according to the present disclosure include bispecific antibodies, whole antibodies, minibodies, domain antibodies, antibody mimetics (or synthetic antibodies), antibody fusions (or antibody conjugates), fragments thereof, and combinations thereof, but are not limited thereto. The structures of various antibodies will be further described later.

In the present disclosure, for example, a "variant" of a peptide, such as an antigen-binding fragment, protein, or antibody, is a peptide in which insertions, deletions, additions and/or substitutions have occurred at one or more amino acid residues compared to other peptide sequences, and may include the fusion peptide. For example, a portion of an antibody may include conservative amino acid substitutions at one or more residues of the heavy or light chain, variable region or CDR sequence.

In relation to antibodies according to the present disclosure, a target antibody may be generated and selected from transgenic animals (for example, transgenic mice) by using hybridoma technology. Such antibodies may be cloned and expressed by using appropriate vectors and host cells, or the antibodies may be harvested from cultured hybridoma cells. In addition, the antibody may be derived from a phage-display library. The phage display technology is a method that mimics an immune selection, in which an antibody repertoire is displayed on the surface of a filamentous bacteriophage and a phage that binds to a target antigen is screened therefrom. This technique may be understood by referring to Examples of the present disclosure or to PCT Publication No. WO 99/10494.

An antibody or antigen-binding fragment thereof may be derived from only a single source, or may be chimeric. A chimeric antibody includes portions derived from two different types of antibodies and is described in more detail below. An antibody or antigen-binding fragment thereof may be produced by hybridoma, recombinant DNA technology, or enzymatic or chemical cleavage of an intact antibody. Unless otherwise stated, the term "antibody" as used herein includes an antibody including two full-length heavy chains and two full-length light chains, and the derivatives, variants, immunologically functional immunoglobulin fragments, and mutants of the antibody, and combinations thereof. For example, the term "antibody" includes, in addition to two full-length heavy chains and two full-length light chains, one or two scFvs, and examples thereof will be described in detail.

The term "antigen-binding fragment" as used herein may refer to a portion of an antibody having a specific binding ability to an antigen ora polypeptide including the same. For example, the antigen-binding fragment may be a portion of an antibody which includes an amino acid residue that interacts with an antigen (for example, an epitope) to provide the antibody a specificity and/or affinity to the antigen, or a polypeptide including the same. The fragment may include at least one CDR present in a full-length light or heavy chain, and in some embodiments, may include a single heavy and/or light chain, or a portion thereof. Such biologically active fragments may be produced by recombinant DNA techniques, or may be produced by, for example, enzymatic or chemical cleavage of intact antibodies.

Immunologically functional immunoglobulin fragments include, but are not limited to, Fab, Fab', F(ab')2, Fv, domain antibodies and single chain antibodies (for example, scFv, Fc-scFv, etc.). The immunologically functional immunoglobulin fragment may be derived from any mammal, including a human, mouse, rat, camel, or rabbit, and is not limited thereto. Functional portions of an antibody, such as one or more of the CDRs described herein, may be covalently connected to a second protein or small molecule compound so as to be used as a targeted therapeutic agent for a specific target.

A "single-chain antibody" as used herein is a single polypeptide chain of an antigen binding region in which the heavy and light chain variable regions are connected by a flexible linker. For example, the single-chain antibody may be at least one selected from scFv in which a heavy chain variable region and a light chain variable region are connected in the form of a single chain, and Fc-scFv in which a heavy chain variable region, a light chain variable region, and Fc are connected in the form of a single chain. For single-chain antibodies, for example, U.S. Pat. No. 5,260,203 may be referred.

The "affinity" as used herein refers to is the strength of the interaction between an antibody or antigen-binding fragment thereof and an antigen, and may be determined depending on the CDR sequence of the antibody or antigen-binding fragment, and/or physicochemical properties of the antibody or antigen-binding fragment properties (hydrophilic/hydrophobicity, electrostatic properties, etc.), characteristics of the antigen such as the size, shape, and/or charge of the antigen, and the like. A method of determining such affinity is known in the art, and may be typically expressed as a dissociation constant (KD), but is not limited thereto.

A "multi-specific antigen binding protein" or "multi-specific antibody" as used herein targets two or more antigens or epitopes.

A "bispecific" antigen binding protein or antibody as used herein is a hybrid antigen binding protein or antibody having two different antigen binding sites. Such a bispecific antibody is a type of multispecific antigen binding protein or multispecific antibody, and may be produced by various known methods, for example, hybridoma fusion or ligation of Fab' fragments or scFv fragments. (See, for example, Songsivilai and Lachmann, Clin. Exp. Immunol. 1990, 79:315-321; Kostelny et al. J. Immunol. 1992, 148:1547-1553, et al.) Two different epitopes, to which the two antigen binding sites of a bispecific antigen binding protein or an antibody bind, may be located on the same or different protein targets.

The Fc-containing bioactive peptide may include an antibody protein in which a heavy chain Fc and an antigen-binding fragment are bound, and for example, the heavy chain Fc may be contained in an IgG, and the antigen-binding fragment may be scFv containing a heavy chain variable region or a single-chain antibody, and may be connected to the C-terminus of the heavy chain Fc.

For example, the Fc-containing bioactive peptide may be an IgG-scFv bispecific antibody in which IgG and scFv are bound. The IgG-scFv bispecific antibody may be a monovalent bispecific antibody in which one scFv binds to IgG or a bivalent bispecific antibody in which two scFvs are bound thereto.

The Fc-containing bioactive peptide may include a peptide drug bound to Fc. Here, the peptide drug may be defined the same as described above in connection with the peptide drug. The peptide drug may be bound to the N-terminus or C-terminus of the Fc of the Fc-containing bioactive peptide. The peptide drug may be bound to the N-terminus of at least one of the two heavy chains of the Fc of the Fc-containing bioactive peptide.

The first Fc-containing bioactive peptide may be an antibody containing immunoglobulin G (hereinafter, IgG), and the second Fc-containing bioactive peptide may be an IgG-scFv bispecific antibody. The first Fc-containing bioactive peptide does not include scFv, and the second Fc-containing bioactive peptide may include one scFv consisting of SEQ ID No. 11 connected to the C-terminus of one of the two heavy chains of Fc.

The first Fc-containing bioactive peptide may be an antibody including immunoglobulin G (hereinafter, IgG), the second Fc-containing bioactive peptide may be an IgG-scFv monovalent bispecific antibody, and the third Fc-containing bioactive peptide may be an IgG-scFv bivalent bispecific antibody. The first Fc-containing bioactive peptide does not include an scFv, and the second Fc-containing bioactive peptide may include one scFv consisting of SEQ ID No. 11 connected to the C-terminus of one of the two heavy chains of Fc, and the third Fc-containing bioactive peptide may include two scFvs consisting of SEQ ID No. 11, respectively connected to the C-termini of both heavy chains of Fc.

The first to third Fc-containing bioactive peptides may be IgG, and the variable region of the IgG antibody may include a human VH3 domain. For example, in this case, the first to third Fc-containing bioactive peptides each have two VH3 domains (in the heavy chain of the variable region) in IgG, but in regions other than the IgG portion, may have different numbers of VH3 domains.

The first to third Fc-containing bioactive peptides may each be IgG, and the variable region of the IgG antibody may not include a human VH3 domain. For example, in this case, in IgG, the first to third Fc-containing bioactive peptides may not have a VH3 domain, and in a region other than the IgG portion, the first to third Fc-containing bioactive peptides may have different numbers of VH3 domains.

When the Fc-containing bioactive peptide includes a human VH3 domain, the human VH3 domain may be included in the heavy chain variable region of the Fc-containing bioactive peptide.

When the Fc-containing bioactive peptide includes a human VH3 domain, one or more antibody or fragment thereof containing a human VH3 domain may be bound to the Fc-containing bioactive peptide. For example, an scFv including a human VH3 domain may be bound to the Fc-containing bioactive peptide.

When each of the first or second Fc-containing bioactive peptide includes a human VH3 domain, the human VH3 domain may be included in the heavy chain variable region of the first and second Fc-containing bioactive peptides, at least one antibody or fragment thereof including a human VH3 domain may be bound to the bioactive peptide.

In the IgG-scFv bispecific antibody, at least one of IgG and scFv may include a human VH3 domain. When each of IgG and scFv includes a human VH3 domain, the human VH3 domain of IgG and the human VH3 domain of the scFv may have identical or different sequences. The IgG-scFv bispecific antibody may have one or more bioactive activities.

When the Fc-containing bioactive peptide includes an IgG antibody, the IgG antibody may include at least one selected from a first heavy chain and a second heavy chain. Here, the first heavy chain may consist of VH-CH1-CH2-CH3-scFv, and the second heavy chain may consist of VH-CH1-CH2-CH3.

To increase the dimerization probability of the first heavy chain and the second heavy chain to facilitate the production of a monovalent bispecific antibody, a specific position of the heavy chain constant region of one heavy chain may be subjected to a hole mutation (for example, T366S, L368A, or Y406V), a specific position of the heavy chain constant region of other heavy chain may be subjected to a knob mutation (for example, T366W). The Fc-containing bioactive peptide may include an anti-α-synuclein IgG antibody or an anti-BACE antibody.

The anti-α-synuclein antibody may include at least one of a first heavy chain or a second heavy chain. For example, the first heavy chain may include a heavy chain variable region of an anti-α-synuclein antibody, a human heavy chain constant region, and an anti-IGF1R antibody or fragment thereof (for example, anti-IGF1R scFv) bound to the C-terminus of the heavy chain constant region, and the second heavy chain includes a heavy chain variable region of an anti-α-synuclein antibody and a human heavy chain constant region, and may not include the anti-IGF1R antibody.

The anti-α-synuclein antibody may include two first heavy chains, or two second heavy chains. In an embodiment, the α-synuclein antibody may include one first heavy chain and one second heavy chain.

The second Fc-containing bioactive peptide may include one first heavy chain and one second heavy chain, the third Fc-containing bioactive peptide may include two first heavy chains, and the first Fc-containing bioactive peptide may include two second heavy chains.

The mixture of Fc-containing bioactive peptides may include a first Fc-containing bioactive peptide in which the anti-IGF1R antibody or fragment thereof is not bound to the C-terminus of each of the two heavy chains of the anti-α-synuclein antibody, a second Fc-containing bioactive peptide in which the anti-IGF1R antibody or fragment thereof binds to the C-terminus of one of the two heavy chains of the anti-α-synuclein antibody, and a third Fc-containing bioactive peptide in which the anti-IGF1R antibody or fragment thereof binds to the C-terminus of each of the two heavy chains of the anti-α-synuclein antibody.

In the present specification, the description of ch11F11 in PCT Publication No. WO2019-117684 applies equally to ch11F11 herein unless contradicted herein, and the description of hu11F11 in PCT Publication No. WO2019/117684 applies equally to hu11F11 herein unless contradicted herein. These PCT publications may be referred to regarding the sequences for ch11F11 and hu11F11.

The bioactive peptide is an anti-α-synuclein antibody including the heavy chain variable region of the anti-α-synuclein antibody of any one selected from ch11F11, ch1E4, anti-BACE, and hu11F11, and the anti-IGF1R antibody or fragment thereof may include an amino acid sequence represented by: the heavy chain variable region sequence of SEQ ID No. 1 and the light chain variable region sequence of SEQ ID No. 2; the heavy chain variable region sequence of SEQ ID No. 3 and the light chain variable region sequence of SEQ ID No. 4; the heavy chain variable region sequence of SEQ ID No. 5 and the light chain variable region sequence of SEQ ID No. 6; the heavy chain variable region sequence of SEQ ID No. 7 and the light chain variable region sequence of SEQ ID No. 8; or the heavy chain variable region sequence of SEQ ID No. 9 and the light chain variable region sequence of SEQ ID No. 10.

According to the method of separating the Fc-containing bioactive peptide of an embodiment, a target Fc-containing bioactive peptide may be easily separated from a mixture of Fc-containing bioactive peptides using affinity chromatography. In particular, according to the method of purifying Fc-containing bioactive peptides according to an embodiment, process simplification can be achieved and bioactive peptides having the same or similar structure can be precisely separated with high purity.

In addition, according to the separation method of the Fc-containing bioactive peptide of an embodiment, the bioactive peptides having the same or similar structure can be precisely separated to a high degree of purity without artificially controlling the affinity with the protein A ligand by introducing a specific mutation into Fc. In addition, according to the separation method of the Fc-containing bioactive peptide of an embodiment, the bioactive peptides may be separated while a wild-type protein A ligand to which a mutation is not introduced, or a protein A ligand of the related art is used. Therefore, according to the preparation method of an embodiment, Fc-containing bioactive peptides may be precisely separated to a high level of purity without using an expensive protein A ligand into which a mutation is introduced to increase affinity with the Fc region. According to another embodiment of the present disclosure, a method of purifying an antibody in the antibody mixture may be provided. The description of the embodiments for the method of purifying the bioactive peptide may be applied to Examples for the method of purifying the antibody, which will be described later, as long as there is no contradiction.

An embodiment of the present disclosure provides a method of purifying an antibody, the method including: (a-1) loading an antibody mixture into a column containing an affinity matrix containing a protein A ligand, wherein the antibody mixture includes a monospecific antibody, a monovalent bispecific antibody in which one antigen-binding fragment including a human VH3 domain binds to the C-terminus of one of two heavy chain constant regions of the monospecific antibody, and a bivalent bispecific antibody in which the antigen-binding fragment binds to the C-terminus of each of two heavy chain constant regions of the monospecific antibody; (b-1) eluting the monospecific antibody by loading an eluate having a first pH range into the column; (c-1) eluting the monovalent bispecific antibody by loading an eluate having a second pH range lower than the first pH range into the column; and (d-1) eluting the bivalent bispecific antibody by loading an eluate having a third pH range lower than the second pH range into the column.

The variable region of the monospecific antibody may or may not include a human VH3 domain.

The antigen-binding fragment may be scFv. The antigen-binding fragment may be scFv including the amino acid sequence of SEQ ID No. 11.

That is, an example of a bispecific antibody according to the present disclosure may include a heavy component and a light chain of an anti-α-synuclein antibody, wherein the heavy component may include (1) the heavy chain of an anti-α-synuclein antibody and (2) the heavy chain and light chain of an anti-IGF1R antibody. In other words, in the bispecific antibody according to the present disclosure, an anti-IGF1R antibody in scFv form may be bound to either or both of the C-terminus of the anti-α-synuclein antibody in IgG form (respectively referred to as monovalent or bivalent).

The first pH range may be 3.4 or more and 5.0 or less, the second pH range may be 3.3 or more and 4.1 or less, and the third pH range may be 3.0 or more and 4.0 or less. For example, the first pH range may be 3.4 or more and 4.5 or less, the second pH range may be 3.3 or more and 4.1 or less, and the third pH range may be 3.0 or more and 4.0 or less.

However, the first to third pH ranges are examples only, and those of ordinary skill in the art can easily derive the first to third pH ranges which vary depending on the type of bioactive peptide with reference to the description of the present specification.

In particular, in the case of an asymmetric heterodimer protein, it is very difficult to remove, in the purification process, a homodimer that may occur in the production process. This is because the differences in affinity and isoelectric point (pi) between the heterodimer and the homodimer is not as large as being suitable for the purification method using an affinity column or an ion exchange column which are generally used in a protein purification process.

In relation to the separation of heterodimeric antibodies, US Patent Registration Publication No. U.S. Pat. No. 8,586,713 B2 or the like discloses a method of increasing the difference in affinity and isoelectric point by artificially substituting the Fc sequence. However, when amino acids are artificially substituted, as described above, immunogenicity may occur. In addition, when the VH3 sequence is present at the same time, the affinity resin needs be used twice, and the monovalent bispecific antibody and the monospecific antibody can be separated, only after the bivalent bispecific antibody is removed first. Therefore, the process is complicated, and thus, the separation process is performed at high costs for a long time.

However, according to the method of purifying an antibody according to an embodiment, a heterodimer can be purified to the level of 85% to 90% or more without the artificial amino acid substitution in a peptide which cannot be purified using affinity chromatography or ion exchange chromatography of the related art due to the small difference in the isoelectric point (for example, 0.1 or less), like in the case of a heterodimer and a homodimer. In addition, according to the separation method of an embodiment, not only the fragment of the antibody, but also the complete antibody including the Fc region can be effectively separated, and can be separated finely according to the number of VH3 domains.

Advantageous Effects of Invention

The method for purifying an Fc-containing bioactive peptide or an antibody according to an embodiment enables the purification of a peptide or an antibody to a high level of purification by using the difference in binding strength of the full domain protein A ligand due to the difference in the number of VH3 domains of the peptides included in the Fc-containing bioactive peptide or the antibody mixture. In addition, in the method of purifying an Fc-containing bioactive peptide or antibody according to an embodiment, there is no need to introduce a specific mutation into Fc or protein A ligand in order to control the binding force between Fc and the protein A ligand, and thus, high-purity proteins may be obtained using a simplified process at low manufacturing costs.

DETAILED DESCRIPTIOIN OF INVENTION

Figure 1:
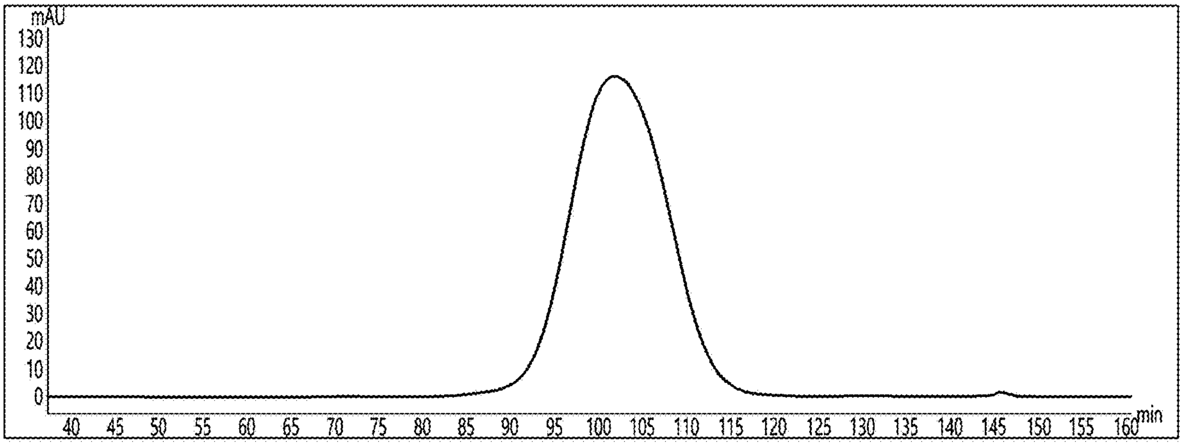
FIG. 1 shows the purification profile of affinity chromatography using a MabSelet Sure resin applied on a bioactive peptide mixture including a monospecific antibody, a monovalent bispecific antibody, and a bivalent bispecific antibody.

Hereinafter, the advantages and features of the present disclosure and methods for achieving the same will be described in detail with reference to the following examples. However, the present disclosure is not limited to the embodiments disclosed below, and may be implemented in various different forms. The present embodiments are provided to make the disclosure of the present invention complete, and to fully inform those of ordinary skill in the art to which the present invention belongs, the scope of the invention, and the present disclosure is defined by the claims only.

Example 1: Preparation of Monovalent Bispecific Antibodies (1) Construction of Monovalent Bispecific Antibody Expression Vector To construct a monovalent bispecific antibody expression vector, the nucleotide sequence of an antibody including the signal sequence was inserted into the multi cloning site (MCS) of the pcDNA3.4 (invitrogen) vector. The expression vector used herein was a monocistronic vector, and a heavy chain expression vector and a light chain expression vector were prepared, separately.

As the heavy chain expression vector, heavy chain expression vector 1 having a first heavy chain sequence and heavy chain expression vector 2 having a second heavy chain sequence were prepared.

In heavy chain expression vector 1, anti-IGF1R scFv (1564, F06, VH5, VH9, VH16, see Table 2) is connected as a linker to the C-terminus of immunoglobulin to which a human heavy chain constant region and a heavy chain variable region of an anti-α-synuclein antibody, such as ch11F11 (see the sequence list of WO2019/117684), ch1E4 (see heavy chain SEQ ID No. 18 and light chain SEQ ID No. 19), or hu11F11 (see the sequence list of WO2019/117684), or anti-BACE (see the sequence of hu2H8v29 in WO2019/094608) antibody, are connected, and a sequence substitution (hole mutation: T366S, L368A, Y406V) has occurred at a specific position in the heavy chain constant region.

In heavy chain expression vector 2, only the heavy chain variable region encoding the anti-α-synuclein antibody or the anti-BACE antibody and a human heavy chain constant region are connected, and a sequence substitution (knob mutation: T366W) has occurred at a specific position in the heavy chain constant region.

In the case of the light chain sequence inserted into the light chain expression vector, the light chain variable region encoding the anti-α-synuclein antibody or the anti-BACE antibody and the human light chain constant region are connected.

In Example 1, the nucleic acid sequence encoding the antibody in heavy chain expression vector 1, heavy chain expression vector 2, and the light chain expression vector is set forth in SEQ ID No. 20 to SEQ ID No. 22.

The amino acid sequence constituting hu11F11×F06, which is an example of the monovalent bispecific antibody according to an embodiment, is shown in Table 1 below.

TABLE 1

| Typical double antibody | Bispecific antibody light chain | Bispecific antibody heavy component | SEQ ID | Double antibody heavy component structure description | Amino acid sequence |
|---|---|---|---|---|---|
| hu11F11 × F06 (monovalent) | Hu11F11-VLv3 4c (WO2019/117684) | hu11F11(ver.2) (M428L)-F06(de2)(StoP) (HC 1, -hole) | SEQ ID No. 12 | hu11F11 (ver.2) (IgG) M428L, HOLE MUTATION | WO2019/117684 |
| | | | | (G4S)3 | SEQ ID No. 14 |
| | | | | F06(de2)(StoP) VL | SEQ ID No. 15 |
| | | | | (G4S)4 | SEQ ID No. 16 |
| | | | | F06(de2)(StoP) VH | SEQ ID No. 17 |

TABLE 1-continued

| Typical double antibody | Bispecific antibody light chain | Bispecific antibody heavy component | SEQ ID | Double antibody heavy component structure description | Amino acid sequence |
|---|---|---|---|---|---|
| | | hu11F11(ver.2) (M428L) (HC 2, -knob) | SEQ ID No. 13 | hu11F11 (ver.2) (IgG) M428L, KNOB MUTATION | WO2019/117684 |

A monovalent bispecific antibody is a heterodimeric form in which an scFv is connected to the C terminus of one of the heavy chain Fc of an anti-α-synuclein antibody or an anti-BACE antibody and scFv is not connected to the other heavy chain Fc.

In general, a combination of knob-knob dimer antibody, a combination of knob-hole dimer antibody, and a combination of hole-hole dimer antibody are all produced in the production of monovalent bispecific antibodies. During the purification process for separation of a pure heterodimer (knob-hole dimer), for the purpose of purification resolution comparison and the use as a control material, a monospecific antibody (150 kd, which is the same size as the knob-knob dimer) and a bivalent bispecific antibody (200 kd, which is the same size as the hole-hole dimer) were additionally cloned.

For purification resolution comparison and the production of a control material required for analysis, in the case of the heavy chain sequence of a monospecific antibody, there are only a heavy chain variable region encoding an anti-α-synuclein antibody or an anti-BACE antibody and a human immunoglobulin heavy chain constant region, and in the case of the heavy chain sequence of the bivalent bispecific antibody, scFv is connected as a linker to the C terminus of the same heavy chain sequence as the single antibody, but no sequence substitution is made in the heavy chain constant region. The monospecific antibody, the bivalent bispecific antibody, and the monovalent bispecific antibody have the same light chain sequence region.

The heavy and light chain variable region sequences of the anti-IGF1R scFvs (1564, F06, VH5, VH9, VH16) used in this Example are shown in Table 2 below.

TABLE 2

| Antibody | Type of sequence | Sequence |
|---|---|---|
| 1564 | Variable heavy chain region sequence (SEQ ID No. 1) | EVQLLESGGGLVQPGGSLRLSCAASGFTFSSYDMSWVR QAPGKCLEWVSAISYDNANTYYADSVKGRFTISRDNSKN TLYLQMNSLRAEDTAVYYCAKGVLTTLMNWFDYWGQGT LVTVSS |
| | Variable light chain region sequence (SEQ ID No. 2) | QSVLTQPPSASGTPGQRVTISCTGSSSNIGSNDVSWYQ QLPGTAPKLLIYANVNRPSGVPDRFSGSKSGTSASLAISG LRSEDEADYYCGAWDDSLNAYVFGCGTKLTVL |
| F06 | Variable heavy chain region sequence (SEQ ID No. 3) | EVQLLESGGGLVQPGGSLRLSCAASGFTFSSYDMSWVR QAPGKCLEWVSAISYDNANTYYADSVKGRFTISRDNSKN TLYLQMNSLRAEDTAVYYCAKGVLTTLMNWFDYWGQGT LVTVSS |
| | Variable light chain region sequence (SEQ ID No. 4) | QSVLTQPPSASGTPGQRVTISCTGSSSNIGSNDVSWYQ QLPGTAPKLLIYANVNRPSGVPDRFSGSKSGTSASLAISG LRSEDEADYYCGTWAGSLNAYVFGCGTKLTVL |
| VH5 | Variable heavy chain region sequence (SEQ ID No. 5) | EVQLLESGGGLVQPGGSLRLSCAASGFTFSSYDMSWVR QAPGKCLEWVSAISGDNASTYYADSVKGRFTISRDNSKN TLYLQMNSLRAEDTAVYYCAKGVLTTLMNWFDSWGQGT LVTVSS |
| | Variable light chain region sequence (SEQ ID No. 6) | QSVLTQPPSASGTPGQRVTISCTGSSSNIGSNDVSWYQ QLPGTAPKLLIYANVNRPSGVPDRFSGSKSGTSASLAISG LRSEDEADYYCGAWDDSLNAYVFGCGTKLTVL |
| VH16 | Variable heavy chain region sequence (SEQ ID No. 7) | EVQLLESGGGLVQPGGSLRLSCAASGFTFSSYDMSWVR QAPGKCLEWVSAISGSNANTYYADSVKGRFTISRDNSKN TLYLQMNSLRAEDTAVYYCAKGVLTTLMNWFDYWGQGT LVTVSS |
| | Variable light chain region sequence (SEQ ID No. 8) | QSVLTQPPSASGTPGQRVTISCTGSSSNIGSNDVSWYQ QLPGTAPKLLIYANVNRPSGVPDRFSGSKSGTSASLAISG LRSEDEADYYCGAWDDSLNAYVFGCGTKLTVL |

TABLE 2-continued

| Antibody | Type of sequence | Sequence |
|---|---|---|
| VH9 | Variable heavy chain region sequence (SEQ ID No. 9) | EVQLLESGGGLVQPGGSLRLSCAASGFTFSSYDMSWVR QAPGKCLEWVSAISGDNGSTYYADSVKGRFTISRDNSK NTLYLQMNSLRAEDTAVYYCAKGVLTTLMNWFDSWGQ GTLVTVSS |
| | Variable light chain region sequence (SEQ ID No. 10) | QSVLTQPPSASGTPGQRVTISCTGSSSNIGSNDVSWYQ QLPGTAPKLLIYANSNRPSGVSDRFSGSKSGTSASLAISG LRSEDEADYYCGAWDDSLNGYVFGCGTKLTVL |

(2) Transient Expression

The prepared vector was subjected to maxi-prep (Qiagen) to secure a large amount of plasmid DNA, and then introduced into the cell as follows. In the case of the production of the monovalent bispecific antibody, hole type heavy chain expression vector DNA, knob type heavy chain expression vector DNA, and light chain expression vector DNA were transduced at the ratio of 0.5:0.5:1, and in the case of the production of the monospecific antibody or the bivalent bispecific antibody, heavy chain expression vector DNA and light chain expression vector DNA were transduced at the ratio of 1:1.

The day before transfection, ExpiCHO™ (Gibco, Cat: A29127) cells were spread at the concentration of 3×10E6 to 4×10E6 viable cells/mL in ExpiCHO™ expression medium (Gibco, Cat: A29100-01), and then, cultured under the conditions of 8% $CO_2$, 37° C., and 120 rpm for 1 day. On the day of DNA transfection, cells that had grown to have an amount of 7×10E6 to 10×10E6 viable cells/mL and the viability of 95% or more, were diluted using fresh medium to an amount of $6\times10^6$ viable cells/mL.

For transfection into the prepared parental cells, ExpiFectamine™ CHO & plasmid DNA complex was prepared using the ExpiFectamine™ CHO transfection kit (Gibco, Cat: A29129). After dispensing cold OptiPRO™ SFM® (Gibco, Cat: 12309019) medium, DNA and ExpiFectamine™ CHO reagent prepared at appropriate concentrations were inoculated and then mixed and leave at room temperature for 5 minutes, and inoculated into parental cells to perform transfection, followed by culturing. The day after transfection, the enhancer included in the ExpiFectamine™ CHO transfection kit and feed were inoculated into the transfected cells, and 5 days later, the feed was additionally inoculated, followed by 10 days of culturing at the conditions of 8% $CO^2$, 37° C., and 120 rpm.

(3) Culture Medium Harvest

In order to obtain a complete produced culture fluid, the culture fluid was transferred to a centrifugation bottle and centrifuged at 4° C., 6500 rpm for 30 minutes, followed by filtering with a filter having a size of 0.2 μm, and the culture fluid after the suspended matter was removed therefrom was obtained as a sample. Thereafter, the purification process was performed.

Example 2: Experimental Preparation for Confirmation of Process Conditions for Purification of Monovalent Bispecific Antibodies by Affinity Chromatography A monovalent bispecific antibody was produced according to the method of Example 1. At this time, regarding the bivalent bispecific antibody, ch11F11 or hu11F11 clone was used as an anti-α-synuclein antibody, and 1564, VH5, VH9, VH16, or F06 clones was used as an anti-IGF-1R antibody, and both of which correspond to a VH3-family antibodies. Thus, each heavy chain variable region contained a VH3 domain.

In actual production, the target antibody, a monovalent bispecific antibody, is mainly produced by the knob-in-hole, and a bivalent bispecific antibody and a monospecific antibody, which are secondary products, are produced in relatively small amounts. However, in the present experiment, in order to more clearly prove the fact that the purification process according to the present disclosure can separate antibodies depending on the difference in affinity according to the number of VH3 domains, a composition with increased concentrations of the bivalent bispecific antibody and the monospecific antibody, which are considered as a by-product in the purification process, that is, an impurity was prepared (that is, by providing more unfavorable conditions for purification), and the purification process was performed on this composition.

Such a composition contains a monospecific antibody, a monovalent bispecific antibody, and a bivalent bispecific antibody at the ratio of 1:3:1 which are prepared in the same manner as in Example 1, except that a knob or a hole is not included. Such a composition includes antibodies isolated by a purification process as follows:

The affinity chromatography was performed using MabSelectSure (GE Healthcare, Cat. No. 17543803) having only the B (Z) domain as a resin to isolate purified substances having Fc.

After equilibration using an equilibration buffer (50 mM Tris-HCl pH 7.2, 100 mM NaCl), the recovered culture fluid was loaded into the column.

Once loading was completed, washing was performed using 3 column volume of an equilibration buffer, and then, elution was performed using 50 mM sodium citrate pH 3.4. The eluate was neutralized to pH 7.0 by adding 1 M Tris-HCl pH 9.0, followed by a 0.2 μm sterilization filter.

Example 3: Comparison of Antibody Purification Effects Using Various Protein a Resins In order to select a protein A resin suitable for purification of a monovalent bispecific antibody, a sample including a ch11F11 monospecific antibody, a ch11F11-F06 monovalent bispecific antibody, and ch11F11-F06 bivalent bispecific antibody was purified using a commercially available protein A column having various specifications and domains as shown in Table 3 below, and the resulting effects were compared.

TABLE 3

| Resin | MabSelect Sure | MabSelect PrismA | Hitrap protein A FF | MabSelect Xtra | Hitrap protein A HP | POROS MabCapture A Select | Absolute High Cap |
|---|---|---|---|---|---|---|---|
| Particle Size (μm) | 85 | 60 | 90 | 75 | 34 | 45 | 35 |
| Protein A domain | B(Z) | B(Z) | full domain | full domain | full domain | full domain | full domain |

The purification method using each resin was described in detail in Examples 3-1 to 3-7.

The purified sample was analyzed by size exclusion-high performance liquid chromatography (SE-HPLC), sodium dodecyl sulfate polyacrylamide gel electrophoresis (SDS-PAGE), or liquid chromatography mass spectrometer (LC/MS) to confirm the purification results.

For SE-HPLC analysis, 40 mM sodium phosphate and 400 mM sodium perchlorate at pH 6.8 were used as a mobile phase, and an analysis sample in a volume of 20 μL was injected at an analysis sample concentration of 1 mg/mL, and the analysis was performed at a flow rate of 0.8 mL/min. Analytical peaks were determined by absorbance at a wavelength of 280 nm. For SDS-PAGE, NuPAGE 4-12% Bis-Tris gel and MOPS running buffer were used for analysis under a non-reducing condition and a reducing condition. In the case of the reducing condition, 5% 2-mercaptoethanol was added to the analysis sample, and the analysis was performed after heating at 70° C. for 10 minutes. For LC/MS analysis, a Waters Acquity Ultra High Performance Liquid Chromatography (UPLC) system and a Waters Synapt G2-S Quadrupole-Time of Flight (Q-TOF) mass spectrometer were used, and the analysis was performed using a PLRP-S 1000 Å BEH S-200 column. Data were analyzed using Waters BiopharmaLynx V.1.3. software.

Example 3-1: MabSelect Sure

The resolution of the sample was confirmed using HiTrap MabSelect Sure (GE Healthcare, Cat. No. 29-0486-84) resin. After equilibration using an equilibration buffer (25 mM citrate/25 mM sodium phosphate, pH 7.0), the sample prepared in Example 1 was loaded into the column. An elution buffer (25 mM citrate/25 mM sodium phosphate, pH 2.5) was used, and a residence time was 5 minutes, and wash conditions included 0%>50%/1 column volume of elution buffer and the range of pH of 7.0 to 5.0. The gradient condition was 50%>100%/30 column volume of elution buffer.

FIG. 1 shows a purification profile of affinity chromatography according to Example 3-1. In FIG. 1, the x-axis is the sample volume and the unit thereof is mL, and the y-axis is the ultra violet (UV) wavelength at 280 nm and the unit thereof is mAu. As shown in FIG. 1, Example 3-1 had only one elution peak. From this, it was confirmed that HiTrap MabSelect Sure resin showed no affinity difference according to the difference in the number of VH3 domains of the peptides present in the sample.

Example 3-2: MabSelect Prisma

The resolution of the sample was confirmed using MabSelect PrismA (GE Healthcare, Cat. No. 17-5199-01). After equilibration using an equilibration buffer (25 mM citrate/25 mM sodium phosphate, pH 7.0), the sample prepared in Example 1 was loaded into the column. An elution buffer (25 mM citrate/25 mM sodium phosphate, pH 2.5) was used, and a residence time was 5 minutes, and wash conditions included 0%>50%/1 column volume elution buffer and the pH of 7.0 to 5.0. The gradient condition was 50%>100%/30 column volume of elution buffer.

Figure 2:
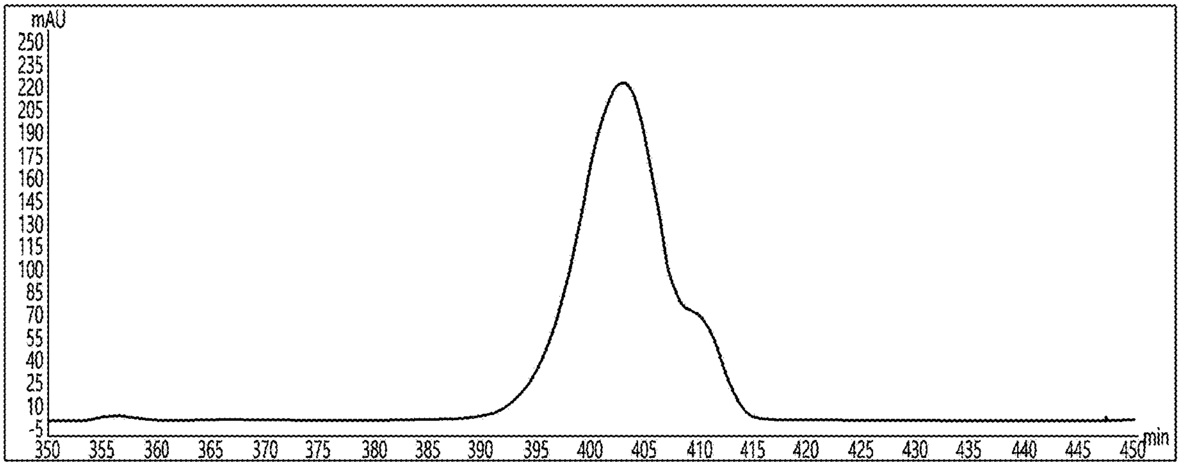
FIG. 2 shows the purification profile of affinity chromatography using a MabSelect PrismA resin applied on a bioactive peptide mixture including a monospecific antibody, a monovalent bispecific antibody, and a bivalent bispecific antibody.

FIG. 2 shows a purification profile of affinity chromatography according to Example 3-2. As shown in FIG. 2, Example 3-2 had only one elution peak. From this, it was confirmed that MabSelect PrismA resin showed no affinity difference according to the difference in the number of VH3 domains of the peptides present in the sample.

Example 3-3: Protein A FF

The resolution of the sample was confirmed using HiTrap protein A FF (GE Healthcare, Cat. No. 17-5079-01). After equilibration using an equilibration buffer (25 mM citrate/25 mM sodium phosphate, pH 7.0), the sample prepared in Example 1 was loaded into the column. An elution buffer (25 mM citrate/25 mM sodium phosphate, pH 2.5) was used, and a residence time was 5 minutes, and wash conditions included 0%>50%/1 column volume elution buffer and the pH of 7.0 to 5.0. The gradient condition was 50%>100%/30 column volume of elution buffer.

Figure 3:
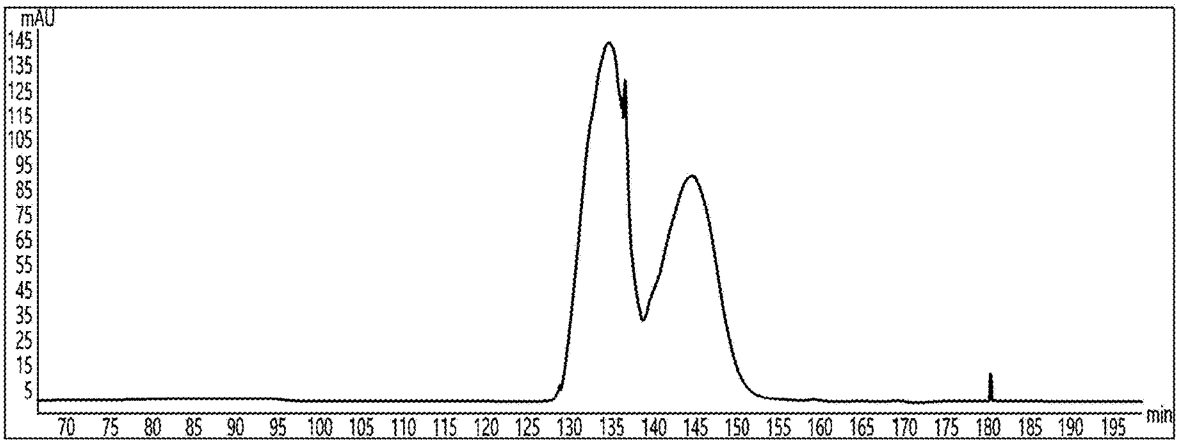
FIG. 3 shows the purification profile of affinity chromatography using a protein An FF resin applied on a bioactive peptide mixture including a monospecific antibody, a monovalent bispecific antibody, and a bivalent bispecific antibody.

FIG. 3 shows a purification profile of affinity chromatography according to Example 3-3. As shown in FIG. 3, peaks of Example 3-3 were not clearly separated. From this, it was confirmed that HiTrap protein A FF resin showed no significant affinity difference according to the difference in the number of VH3 domains of the peptides present in the sample.

Example 3-4: MabSelect Xtra

The resolution of the sample was confirmed using MabSelect Xtra (GE Healthcare, Cat. No. 17-5269-07). After equilibration using an equilibration buffer (25 mM citrate/25 mM sodium phosphate, pH 7.0), the sample prepared in Example 1 was loaded into the column. An elution buffer (25 mM citrate/25 mM sodium phosphate, pH 2.5) was used, and a residence time was 5 minutes, and wash conditions included 0%>50%/1 column volume elution buffer and the pH of 7.0 to 5.0. The gradient condition was 50%>100%/30 column volume of elution buffer.

Figure 4:
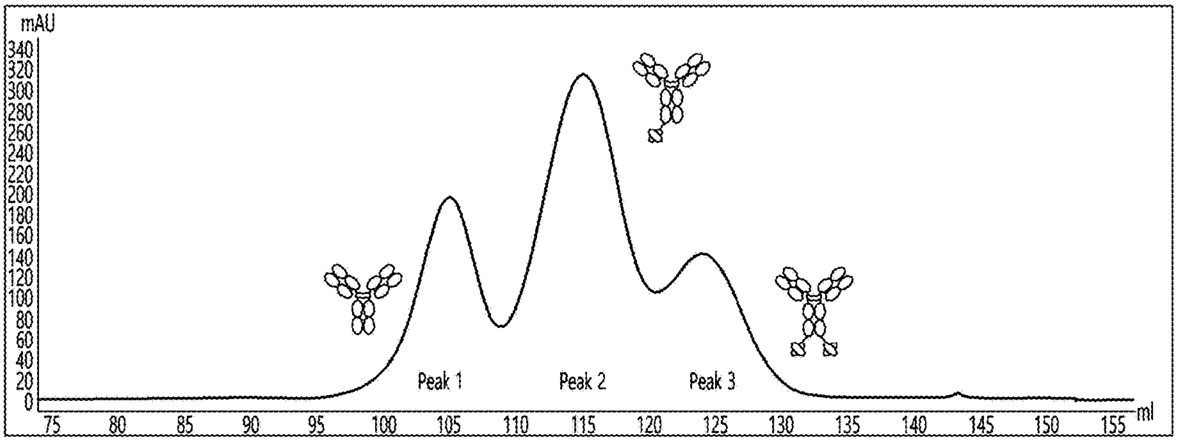
FIG. 4 shows the purification profile of affinity chromatography using a MabSelect Xtra resin applied on a bioactive peptide mixture including a monospecific antibody, a monovalent bispecific antibody, and a bivalent bispecific antibody.
Figure 5:
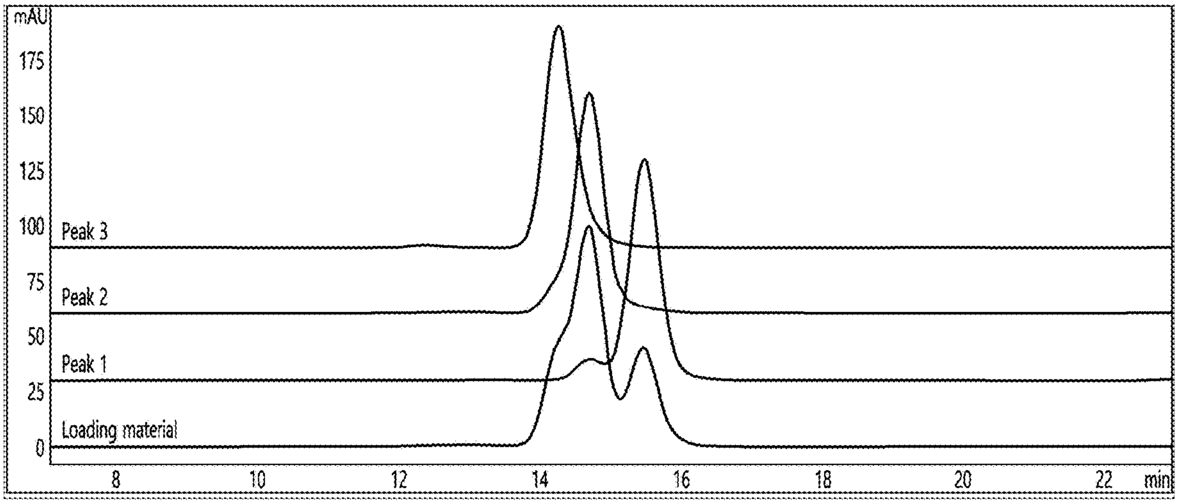
FIG. 5 shows SE-HPLC analysis of the purification results obtained by applying a MabSelect Xtra resin on a bioactive peptide mixture including a monospecific antibody, a monovalent bispecific antibody and a bivalent bispecific antibody.
Figure 6:
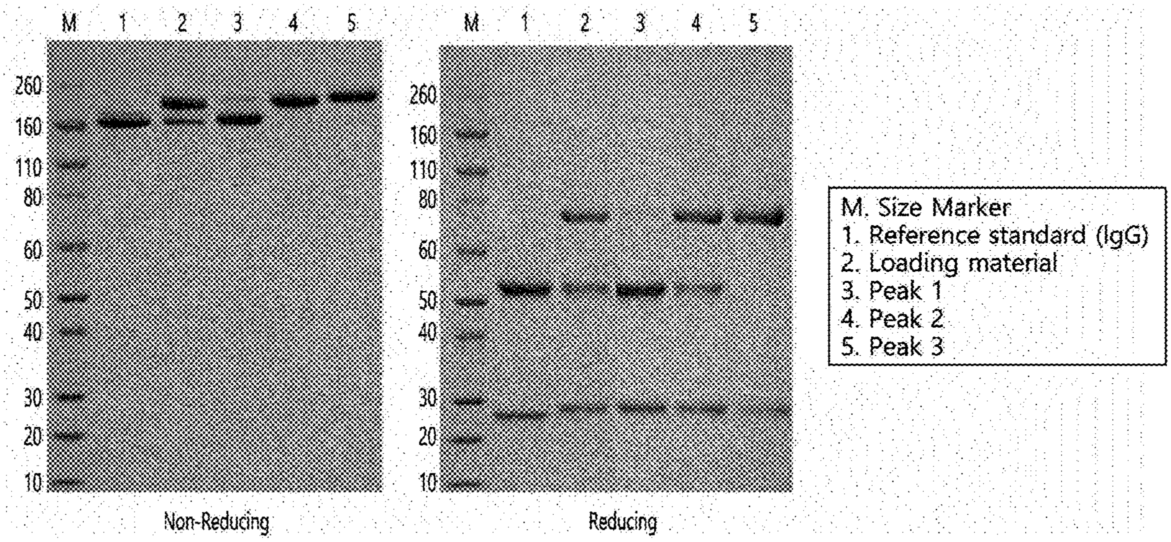
FIG. 6 shows SDS-PAGE analysis of the purification results obtained by applying a MabSelect Xtra resin on a bioactive peptide mixture including a monospecific antibody, a monovalent bispecific antibody and a bivalent bispecific antibody.

FIG. 4 shows the purification profile of affinity chromatography according to Example 3-4, and SE-HPLC and SDS-PAGE results are shown in FIGS. 5 and 6, respectively. As confirmed in FIG. 4, three peaks were identified in the pH range of the elution buffer. Specifically, at a relatively high pH, a monospecific antibody with a small number (two) of VH3 domains was eluted first (Peak 1), and as the pH was lowered, a monovalent bispecific antibody having three VH3 domains was eluted, and then, at further lower pH, the bivalent bispecific antibody with the largest number (four)

of VH3 domains was eluted last. From this, it was confirmed that the MabSelect Xtra resin showed a difference in affinity according to the difference in the number of VH3 domains of the peptides present in the sample, and that ch11F11-F06 could be selectively purified according to the difference in affinity. Other clone combinations showed these results as well.

In addition, through the SE-HPLC and SDS-PAGE results according to FIGS. 5 and 6, it was reconfirmed that the peptides separated by affinity chromatography corresponded to the monospecific antibody, the monovalent bispecific antibody, and the bivalent bispecific antibody, respectively.

Example 3-5: Protein A HP

The resolution of the sample was confirmed using HiTrap protein A HP (GE Healthcare, Cat. No. 17-0402-01). After equilibration using an equilibration buffer (25 mM citrate/25 mM sodium phosphate, pH 7.0), the sample prepared in Example 1 was loaded into the column. An elution buffer (25 mM citrate/25 mM sodium phosphate, pH 2.5) was used, and a residence time was 5 minutes, and wash conditions included 0%>50%/1 column volume elution buffer and the pH of 7.0 to 5.0. The gradient condition was 50%>100%/30 column volume of elution buffer.

Figure 7:
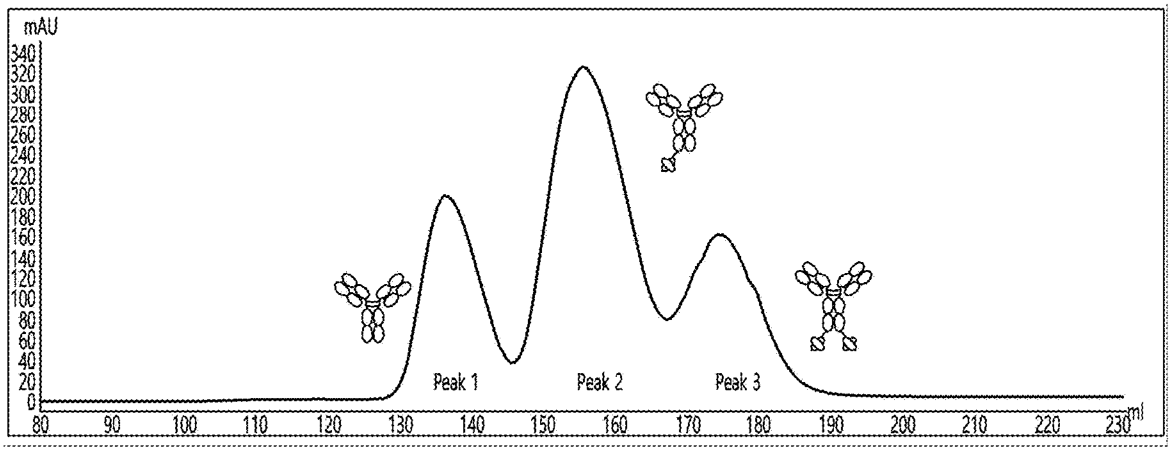
FIG. 7 shows the purification profile of affinity chromatography using a protein A HP resin applied on a bioactive peptide mixture including a monospecific antibody, a monovalent bispecific antibody, and a bivalent bispecific antibody.
Figure 8:
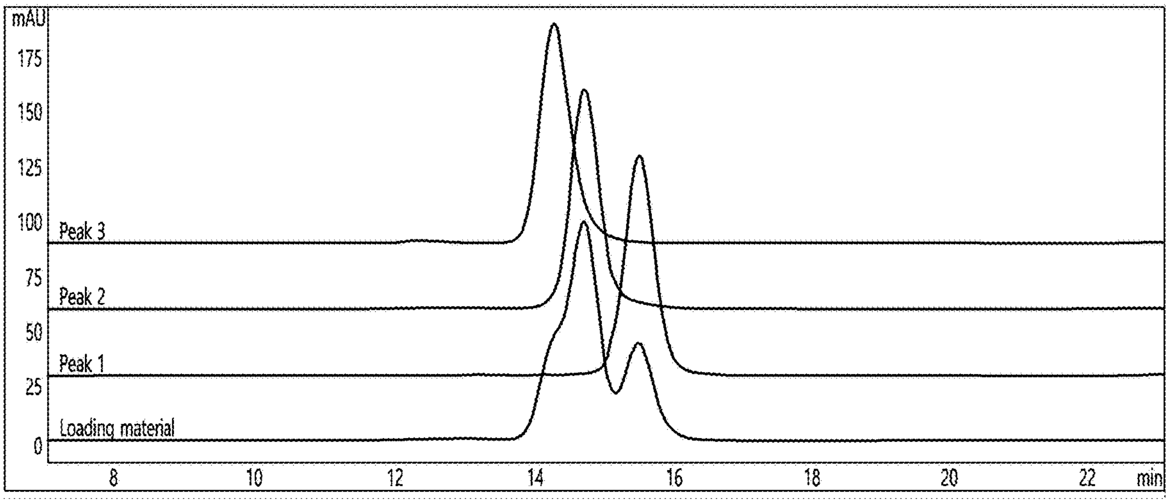
FIG. 8 shows SE-HPLC analysis of the purification results obtained by applying a protein A HP resin on a bioactive peptide mixture including a monospecific antibody, a monovalent bispecific antibody and a bivalent bispecific antibody.
Figure 9:
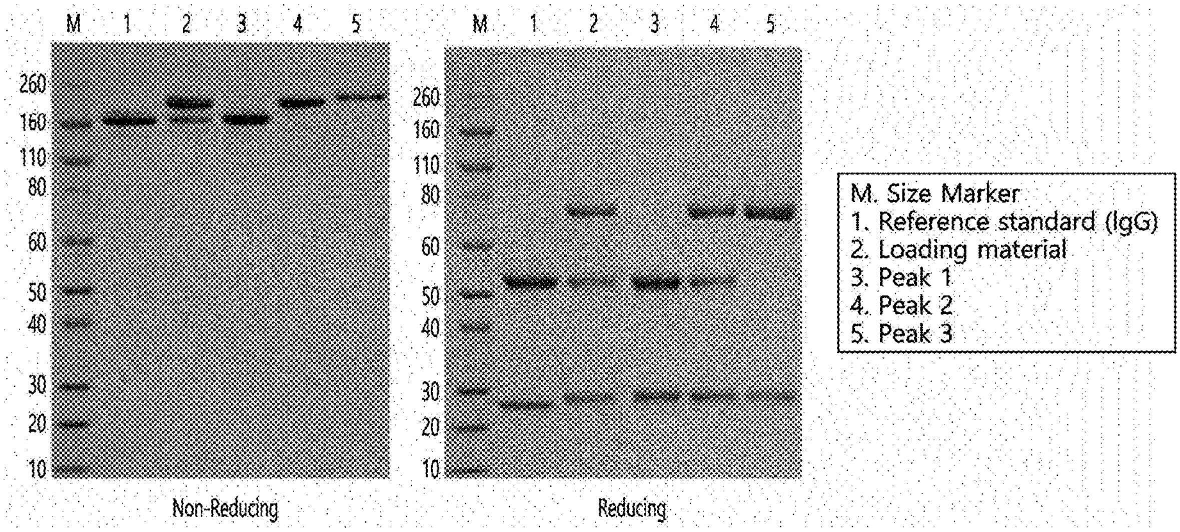
FIG. 9 shows SDS-PAGE analysis of the purification results obtained by applying a protein A HP resin on a bioactive peptide mixture including a monospecific antibody, a monovalent bispecific antibody and a bivalent bispecific antibody.

FIG. 7 shows the purification profile of affinity chromatography according to Example 3-5, and SE-HPLC and SDS-PAGE results are shown in FIGS. 8 and 9, respectively. As confirmed in FIG. 7, three peaks were identified in the pH range of the elution buffer. Specifically, at a relatively high pH, a monospecific antibody with a small number (two) of VH3 domains was eluted first (Peak 1), and as the pH was lowered, a monovalent bispecific antibody having three VH3 domains was eluted, and then, at further lower pH, the bivalent bispecific antibody with the largest number (four) of VH3 domains was eluted last. From this, it was confirmed that the HiTrap protein A HP resin showed a difference in affinity according to the difference in the number of VH3 domains of the peptides present in the sample, and that ch11F11-F06 could be selectively purified according to the difference in affinity. Other clone combinations showed these results as well.

In addition, through the SE-HPLC and SDS-PAGE results according to FIGS. 8 and 9, it was reconfirmed that the peptides separated by affinity chromatography corresponded to the monospecific antibody, the monovalent bispecific antibody, and the bivalent bispecific antibody, respectively.

Example 3-6: POROS MabCapture A Select

The resolution of the sample was confirmed using POROS MabCapture A Select (Thermo Fisher SCIENTIFIC, Cat. No. A26458). After equilibration using an equilibration buffer (25 mM citrate/25 mM sodium phosphate, pH 7.0), the sample prepared in Example 1 was loaded into the column. An elution buffer (25 mM citrate/25 mM sodium phosphate, pH 2.5) was used, and a residence time was 5 minutes, and wash conditions included 0%>50%/1 column volume elution buffer and the pH of 7.0 to 5.0. The gradient condition was 50%>100%/30 column volume of elution buffer.

Figure 10:
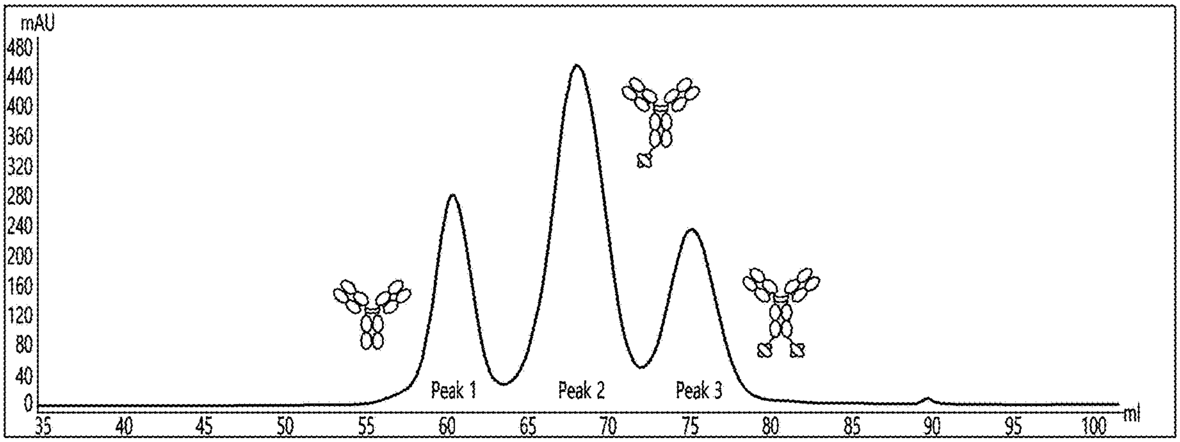
FIG. 10 shows the purification profile of affinity chromatography using a POROS MabCapture A Select resin applied on a bioactive peptide mixture including a monospecific antibody, a monovalent bispecific antibody, and a bivalent bispecific antibody.
Figure 11:
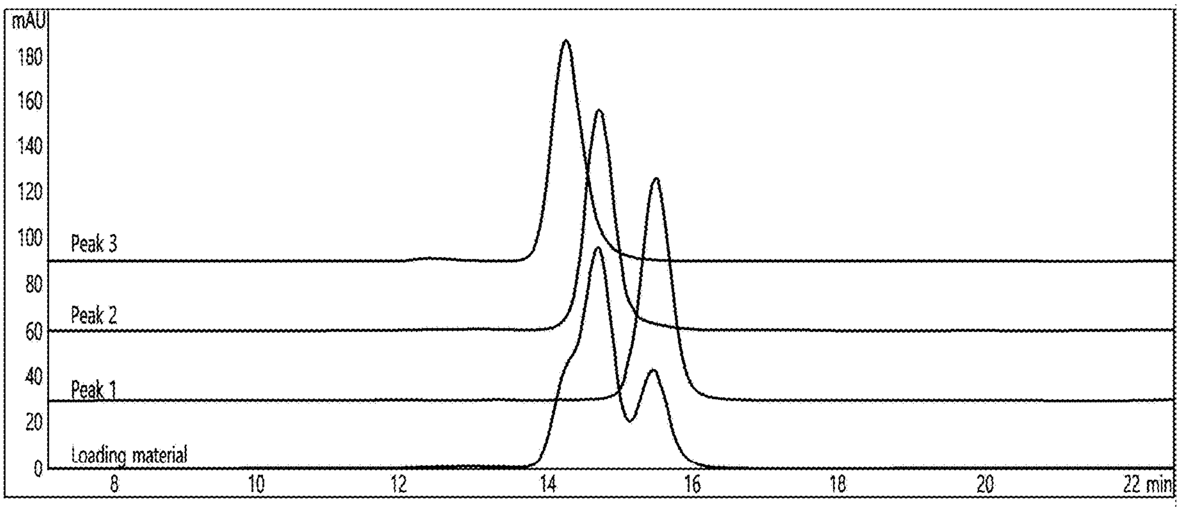
FIG. 11 shows SE-HPLC analysis of the purification results obtained by applying a POROS MabCapture A Select resin on a bioactive peptide mixture including a monospecific antibody, a monovalent bispecific antibody and a bivalent bispecific antibody.
Figure 12:
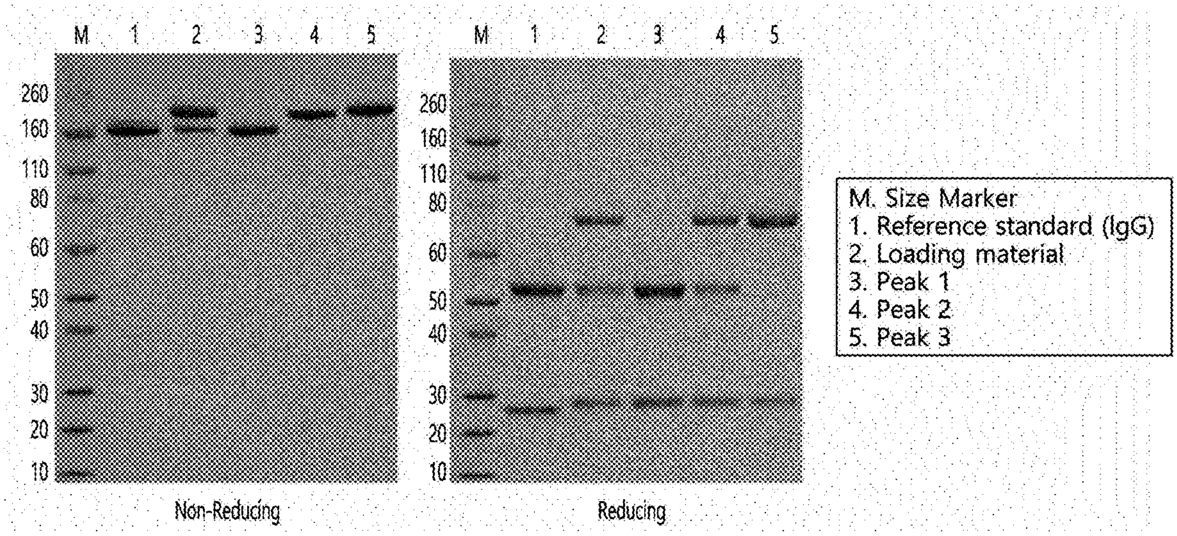
FIG. 12 shows SDS-PAGE analysis of the purification results obtained by applying a POROS MabCapture A Select resin on a bioactive peptide mixture including a monospecific antibody, a monovalent bispecific antibody and a bivalent bispecific antibody.

FIG. 10 shows the purification profile of affinity chromatography according to Example 3-6, and SE-HPLC and SDS-PAGE results are shown in FIGS. 11 and 12, respectively. As confirmed in FIG. 10, three peaks were identified in the pH range of the elution buffer. Specifically, at a relatively high pH, a monospecific antibody with a small number (two) of VH3 domains was eluted first (Peak 1), and as the pH was lowered, a monovalent bispecific antibody having three VH3 domains was eluted, and then, at further lower pH, the bivalent bispecific antibody with the largest number (four) of VH3 domains was eluted last. From this, it was confirmed that the POROS MabCapture A Sele resin showed a difference in affinity according to the difference in the number of VH3 domains of the peptides present in the sample, and that ch11F11-F06 could be selectively purified according to the difference in affinity. Other clone combinations showed these results as well.

In addition, through the SE-HPLC and SDS-PAGE results according to FIGS. 11 and 12, it was reconfirmed that the peptides separated by affinity chromatography corresponded to the monospecific antibody, the monovalent bispecific antibody, and the bivalent bispecific antibody, respectively.

Example 3-7: Absolute High Cap

The resolution of the sample was confirmed using AbSolute High Cap (AGC). After equilibration using an equilibration buffer (25 mM citrate/25 mM sodium phosphate, pH 7.0), the sample prepared in Example 1 was loaded into the column. An elution buffer (25 mM citrate/25 mM sodium phosphate, pH 2.5) was used, and a residence time was 5 minutes, and wash conditions included 0%>50%/1 column volume elution buffer and the pH of 7.0 to 5.0. The gradient condition was 50%>100%/30 column volume of elution buffer.

Figure 13:
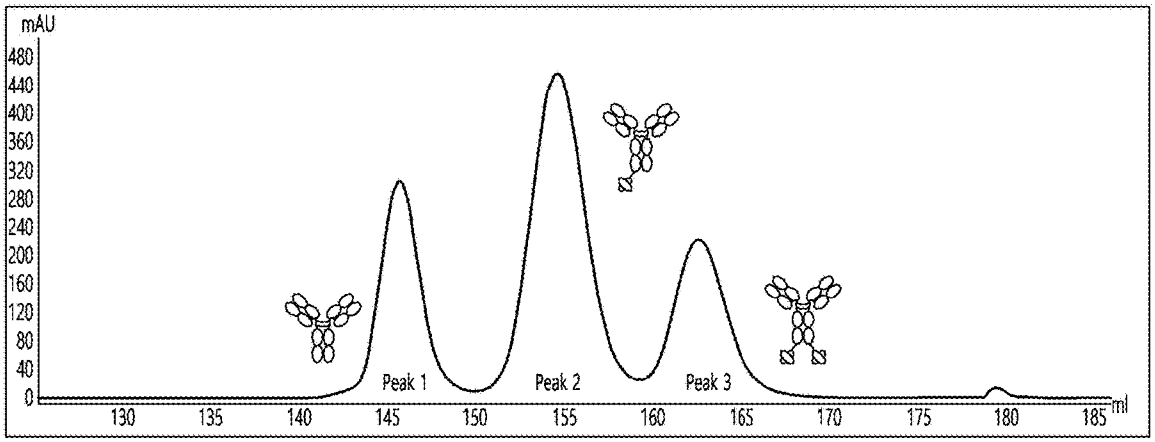
FIG. 13 shows the purification profile of affinity chromatography using an AbSolute High Cap resin applied on a bioactive peptide mixture including a monospecific antibody, a monovalent bispecific antibody, and a bivalent bispecific antibody.
Figure 14:
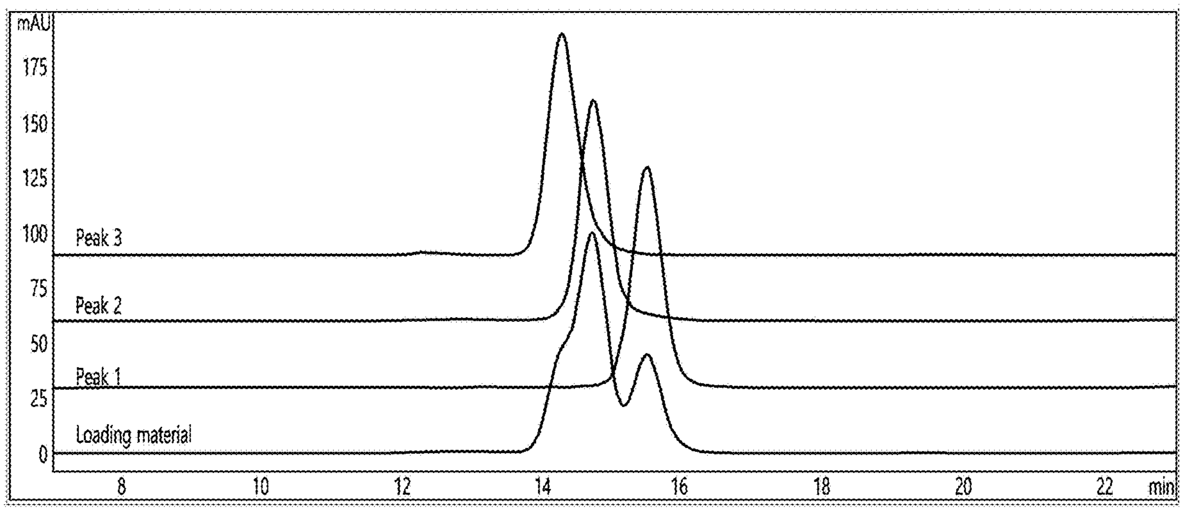
FIG. 14 shows SE-HPLC analysis of the purification results obtained by applying an AbSolute High Cap resin on a bioactive peptide mixture including a monospecific antibody, a monovalent bispecific antibody and a bivalent bispecific antibody.
Figure 15:
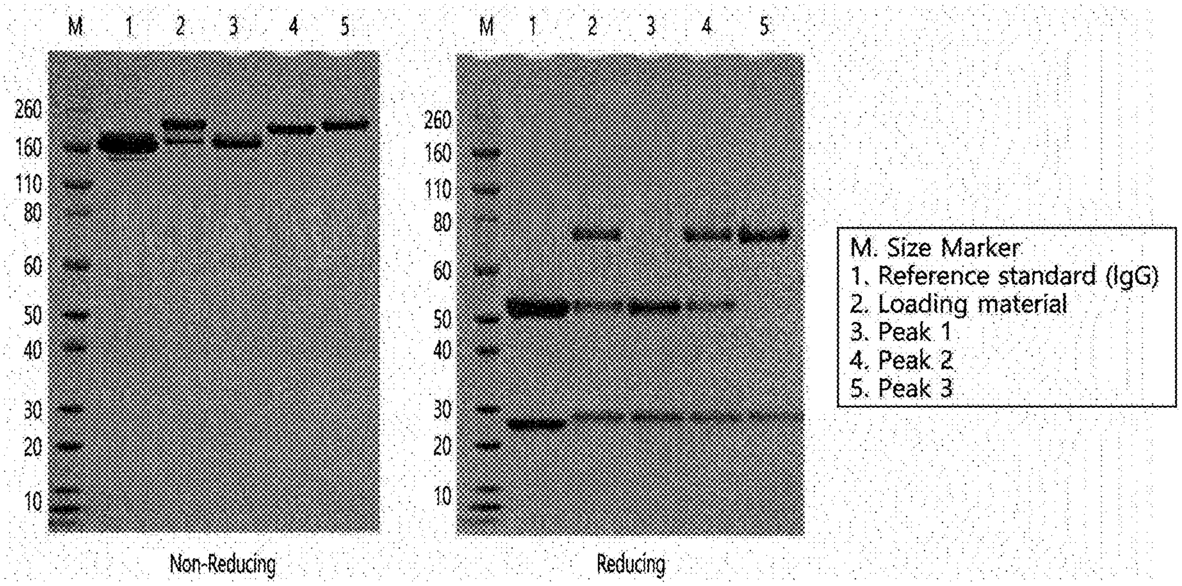
FIG. 15 shows SDS-PAGE analysis of the purification results obtained by applying an AbSolute High Cap resin on a bioactive peptide mixture including a monospecific antibody, a monovalent bispecific antibody and a bivalent bispecific antibody.

FIG. 13 shows the purification profile of affinity chromatography according to Example 3-6, and SE-HPLC and SDS-PAGE results are shown in FIGS. 14 and 15, respectively. As confirmed in FIG. 13, three peaks were identified in the pH range of the elution buffer. Specifically, at a relatively high pH, a monospecific antibody with a small number (two) of VH3 domains was eluted first (Peak 1), and as the pH was lowered, a monovalent bispecific antibody having three VH3 domains was eluted, and then, at further lower pH, the bivalent bispecific antibody with the largest number (four) of VH3 domains was eluted last. From this, it was confirmed that the AbSolute High Cap resin showed a difference in affinity according to the difference in the number of VH3 domains of the peptides present in the sample, and that ch11F11-F06 could be selectively purified according to the difference in affinity. Other clone combinations showed these results as well.

In addition, through the SE-HPLC and SDS-PAGE results according to FIGS. 14 and 15, it was reconfirmed that the peptides separated by affinity chromatography corresponded to the monospecific antibody, the monovalent bispecific antibody, and the bivalent bispecific antibody, respectively.

Summary of Purification Results of Examples 3-1 to 3-7

The pH concentration gradients of the elution buffers at which peaks of Examples 3-4 to 3-7 appeared are as shown in Table 4.

TABLE 4

| Example | Peak 1 Start pH | Peak 1 End pH | Peak 2 End pH | Peak 3 End pH |
|---|---|---|---|---|
| Example 3-4 | 3.86 | 3.58 | 3.39 | 3.26 |
| Example 3-5 | 3.99 | 3.77 | 3.54 | 3.36 |

TABLE 4-continued

| Example | Peak 1 Start pH | Peak 1 End pH | Peak 2 End pH | Peak 3 End pH |
|---|---|---|---|---|
| Example 3-6 | 3.97 | 3.73 | 3.53 | 3.36 |
| Example 3-7 | 3.85 | 3.59 | 3.38 | 3.21 |

The purification results of Examples 3-1 to 3-7 are summarized and described in detail in Table 5.

TABLE 5

| Resin | MabSelect Sure | MabSelect PrismA | Hitrap Protein A FF | MabSelect Xtra | Hitrap Protein A HP | POROS MabCapture A Select | Absolute High Cap |
|---|---|---|---|---|---|---|---|
| Resolution* [I-IV] (Peak 1-2/ Peak 2-3) | I | I | I | II (1.08/0.62) | II (1.01/0.91) | III (1.30/1.08) | IV (1.53/1.21) |
| Alkaline stability [I-IV] | IV | IV | II | II | I | III | IV |
| SE-HPLC Purity (%) | Not applicable | Not applicable | Not applicable | 85.7 | 94.9 | 95.2 | 97.7 |
| Recovery (%)** | | | | 99 | 100 | 96 | 99 |
| Monovalent Yield (%)*** | | | | 73.3 | 79.3 | 76.5 | 79.2 |
| Scalability | Yes | Yes | Yes | Yes | No | Yes | Yes |

The resolution (Rs), recovery yield, and monovalent antibody yield of each example were calculated as follows.

$$Rs = 1.18\frac{(t_{R_2} - t_{R_1})}{(W_{1/2_2} + W_{1/2_1})} *$$

tR1: retention time of peak 1.
tR2: retention time of peak 2
$W½_1$: Width at half height of peak 1
$W½_2$: Width at half height of peak 2

**Recovery (%)=Output (mg)/Input (mg)×100

***Monovalent Yield (%)=Monovalent Output (mg)×Purity (%)/Monovalent Input (mg)×Purity (%)×100

The experiments showed that only the columns used in Examples 3-4 to 3-7 showed affinity differences according to the number of VH3 domains included in the peptide. As a result, it was confirmed that the monospecific antibody, the monovalent bispecific antibody, and the bivalent bispecific antibody were effectively separated according to the pH concentration gradient. Specifically, the antibodies isolated in Examples 3-4 to 3-7 have 2, 3, and 4 VH3 domains which vary depending on the presence and number of anti-IGF1R scFv connected to the C-terminus of Fc of the monospecific antibody having a VH3 domain in a variable region thereof, and in the case of the columns used in Examples 3-4 to 3-7, since the protein A resin has a full domain, the difference in the number of VH3 domains of the antibodies is recognized precisely and thus antibodies were effectively separated. Compared to improved columns such as MabSelect Sure and MabSelect PrismA, which are generally more preferred due to the use of specific domain B(Z) alone to improve Fc binding affinity and alkaline stability, according to the present disclosure, a resin containing protein A of the related art (a special mutation is not introduced) is effective for the separation of peptides according to the number of VH3 domains from a peptide mixture containing a VH3 domain.

Example 4: Analysis of Antibody Purity from Culture Fluid

Using POROS A 20 μm (Thermo fisher, Cat. No. 1-5022-26), it was confirmed whether the target Fc-containing bioactive peptide could be analyzed even when the culture fluid was directly used without the purification of protein A. After equilibration using an equilibration buffer (25 mM citrate/25 mM sodium phosphate pH 7.0), the culture fluid (Harvested Cell Culture Fluid) was directly loaded. Unbound wash was performed using 2 column volume of equilibration buffer, an elution buffer (25 mM citrate/25 mM sodium phosphate pH 2.5) was used, the residence time was 1 minute, and the gradient condition was used where the elution buffer was 50%>100%/30 column volume. The same method was used to analyze a sample which had been pre-purified with protein A, and the obtained results was compared.

Figure 16:
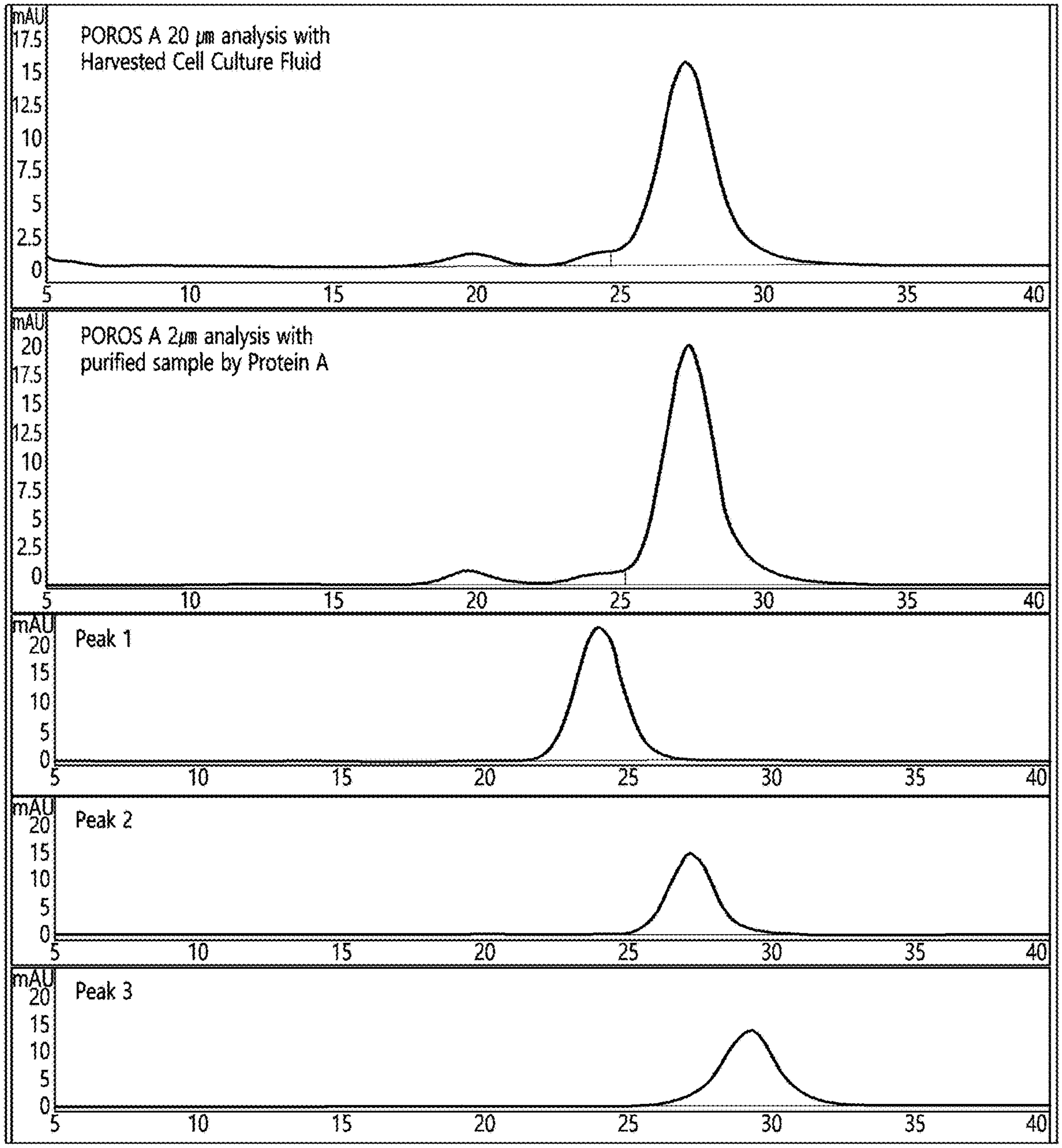
FIG. 16 shows the analysis profile of each of the culture fluid produced by the transient method (Harvested Cell Culture Fluid) and the sample obtained by purifying the culture fluid with protein A, obtained using a POROS A 20 μm analysis column. Peak 1, peak 2, and peak 3 respectively indicate retention time of the purified monospecific antibody, the purified monovalent bispecific antibody, and the purified bivalent bispecific antibody after loaded into a POROS A 20 μm analysis column.

FIG. 16 shows an analysis profile of affinity chromatography according to Example 4. As shown in FIG. 16, it was confirmed that the results of directly analyzing the culture fluid without going through the protein A column and the results of analyzing the sample pre-purified with protein A were very similar to each other as 90.3% and 90.5%, respectively, and the elution profile and the resolution were also similar to each other.

From these results, it was confirmed that, according to the separation method of an embodiment, peptides can be separated and analyzed with excellent resolution even without primary purification of the transient culture with protein A. Therefore, according to the separation method according to an embodiment, even when the number of candidate cell lines is large in the initial stage of cell line development, the culture fluid can be directly used to identify the ratio and purity of an antibody without the primary purification process.

Example 5: Purification of Various Asymmetric Polypeptides

Example 5-1: IgG(VH3(+))-scFv(VH3+)

The resolution of the sample was confirmed using the protein A resin used in Example 3. All protein A resins having the confirmed resolution shown in Table 5 may be used as the protein A resin. As an example, POROS Mab-Capture A Select (Thremo Fisher SCIENTIFIC, Cat. No. A26458) was used for purification. As a sample for purification, a mixture including a monospecific antibody having two VH3 domains (hu11F11) and a monovalent bispecific antibody having three VH3 domains (hu11F11-F06) generated according to the method of Example 1 was used.

Figure 17:
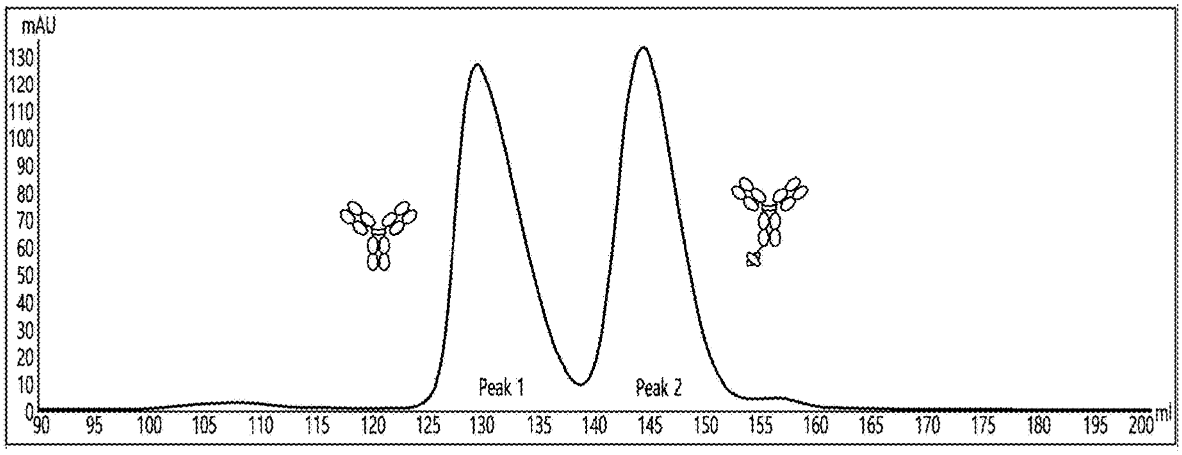
FIG. 17 shows the purification profile of affinity chromatography using POROS MabCapture A Select resin applied on a bioactive peptide mixture containing hu11F11 and hu11F11-F06.
Figure 18:
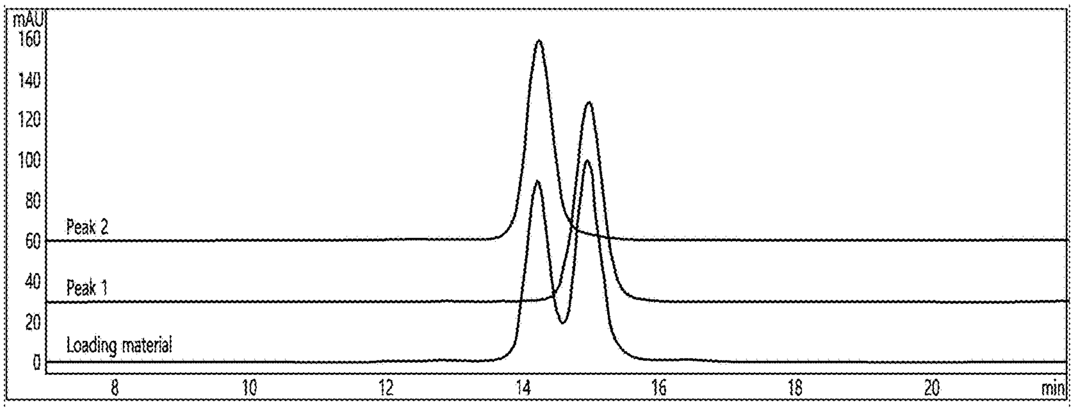
FIG. 18 shows SE-HPLC analysis of the purification results obtained by applying a POROS MabCapture A Select resin on a bioactive peptide mixture including hu11F11 and hu11F11-F06.
Figure 19:
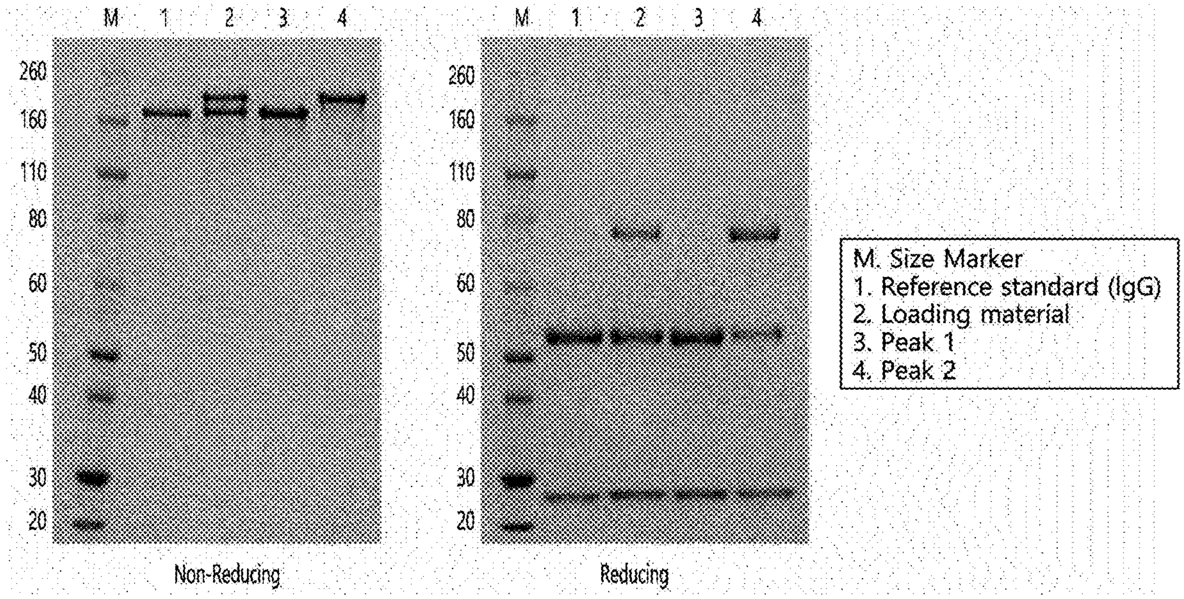
FIG. 19 shows SDS-PAGE analysis of the purification results obtained by applying a POROS MabCapture A Select resin on a bioactive peptide mixture including hu11F11 and hu11F11-F06.

After equilibration using an equilibration buffer (25 mM citrate/25 mM sodium phosphate, pH 7.0), the sample was loaded into the column. An elution buffer (25 mM citrate/25 mM sodium phosphate, pH 2.5) was used, and a residence time was 6 minutes, and wash conditions included 0%>50%/1 column volume elution buffer and the pH of 7.0 to 5.0. The gradient condition was 50%>100%/30 column volume of elution buffer. FIG. 17 shows the purification profile of affinity chromatography, and SE-HPLC and SDS-PAGE results are shown in FIGS. 18 and 19, respectively.

As a result of applying the pH gradient of the elution buffer, two peaks appeared as shown in FIG. 17. Specifically, at a relatively high pH, a monospecific antibody with a small number of VH3 domains (two) was eluted first (Peak 1), and as the pH was lowered, a monovalent bispecific antibody having three VH3 domains was eluted (Peak 2). These results were reconfirmed from the SE-HPLC and SDS-PAGE results shown in FIGS. 18 and 19.

Example 5-2. IgG(VH3(−))-scFv(VH3+)

The resolution of the sample was confirmed using the protein A resin used in Example 3. All protein A resins having the confirmed resolution shown in Table 5 may be used as the protein A resin. As an example, POROS Mab-Capture A Select (Thremo Fisher SCIENTIFIC, Cat. No. A26458) was used for purification. As a sample for purification, a mixture including a monospecific antibody having no VH3 domain (ch1E4 or anti-BACE) and a monovalent bispecific antibody having one VH3 domain (ch1E4-F06 or anti-BACE-F06), both of which are prepared by the method of Example 1 except using anti-BACE antibody that does not contain VH3 domain in the variable region of IgG, was used.

Figure 22:
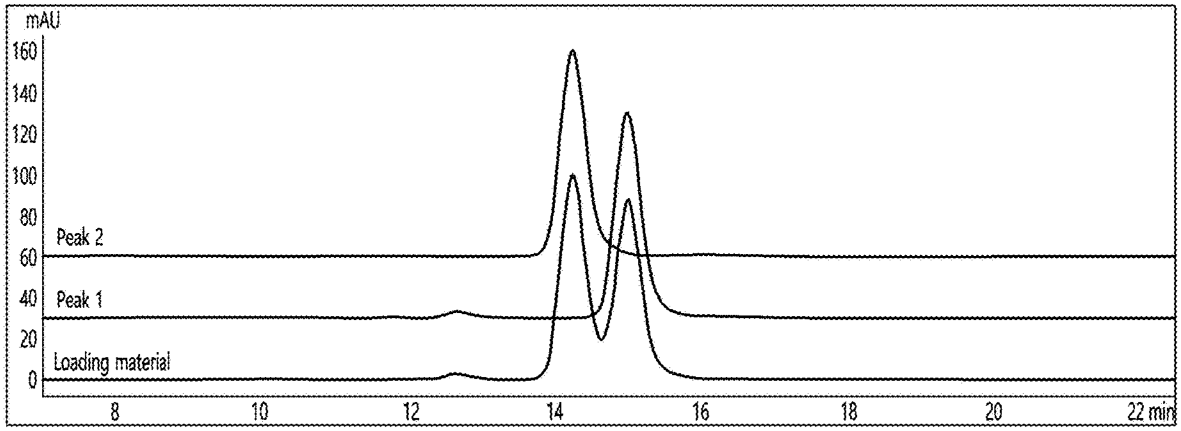
FIG. 22 shows SE-HPLC analysis of the purification results obtained by applying a POROS MabCapture A Select resin on a bioactive peptide mixture including ch1 E4 and ch1E4-F06.
Figure 23:
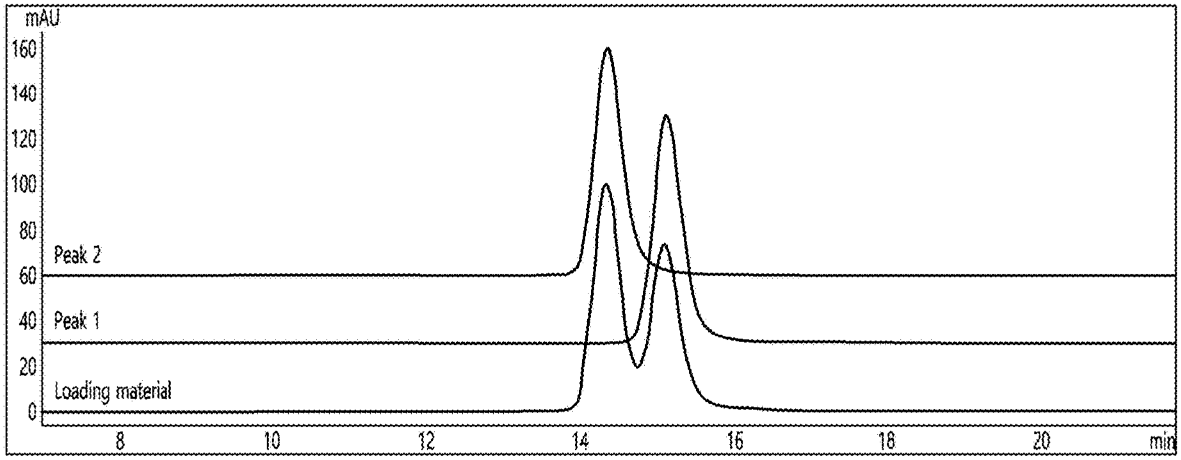
FIG. 23 shows SE-HPLC analysis of the purification results obtained by applying a POROS MabCapture A Select resin on a bioactive peptide mixture including anti-BACE and anti-BACE-F06.
Figure 24:
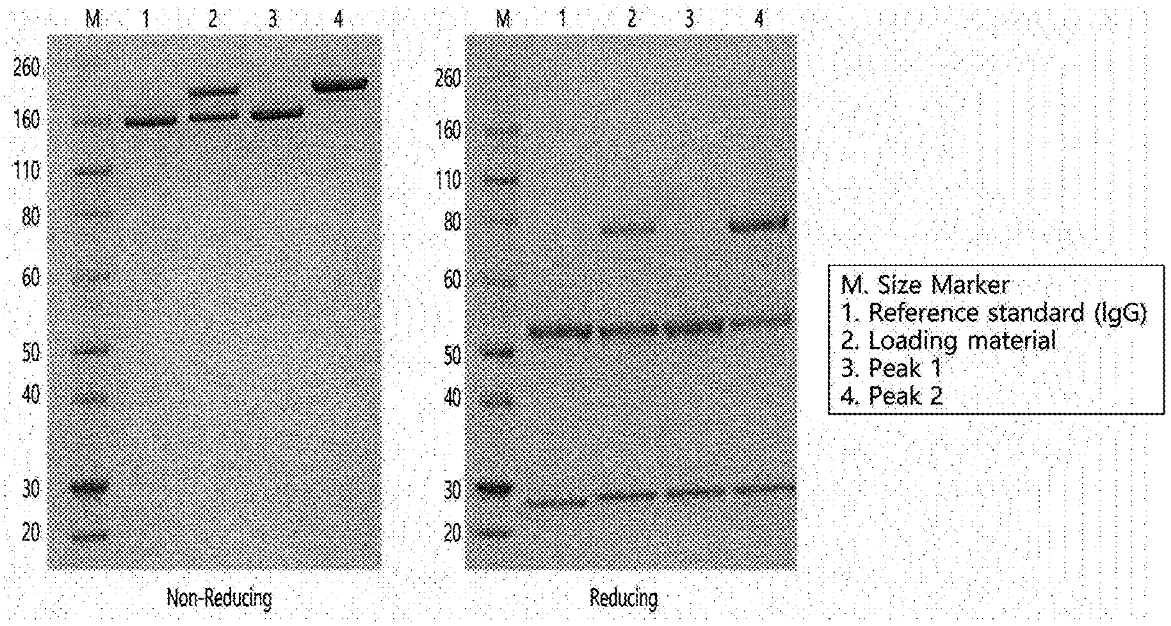
FIG. 24 shows SE-HPLC analysis of the purification results obtained by applying a POROS MabCapture A Select resin on a bioactive peptide mixture including ch1E4 and ch1E4-F06.
Figure 25:
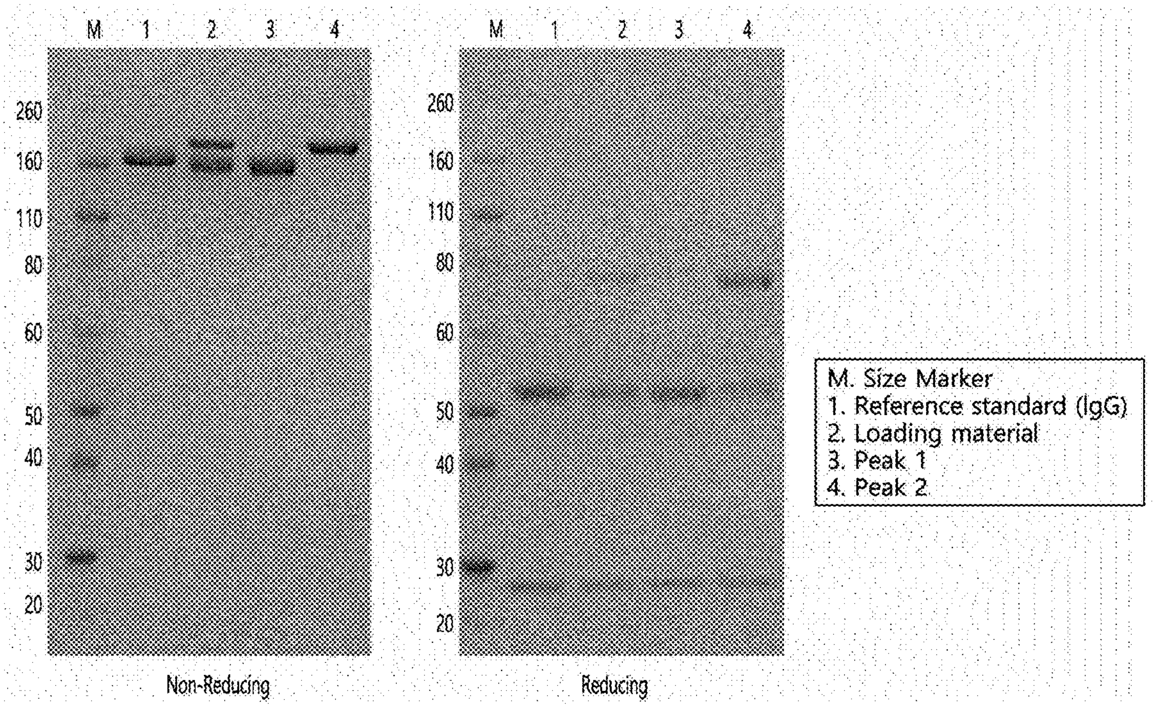
FIG. 25 shows SDS-PAGE analysis of the purification results obtained by applying a POROS MabCapture A Select resin on a bioactive peptide mixture including anti-BACE and anti-BACE-F06.

After equilibration using an equilibration buffer (25 mM citrate/25 mM sodium phosphate, pH 7.0), the sample was loaded into the column. An elution buffer (25 mM citrate/25 mM sodium phosphate, pH 2.5) was used, and a residence time was 6 minutes, and wash conditions included 0%>50%/1 column volume elution buffer and the pH of 7.0 to 5.0. The gradient condition was 50%>100%/30 column volume of elution buffer. The elution peaks of affinity chromatography are shown in FIGS. 20 and 21, the SE-HPLC results are shown in FIGS. 22 and 23, and the SDS-PAGE results are shown in FIGS. 24 and 25.

Figure 20:
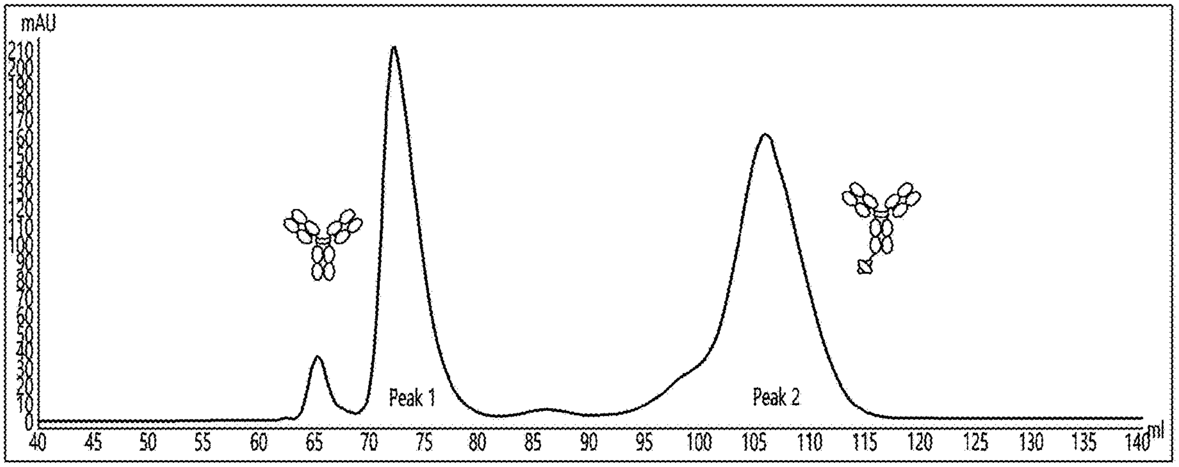
FIG. 20 shows the purification profile of affinity chromatography using POROS MabCapture A Select resin applied on a bioactive peptide mixture containing ch1E4 and ch1E4-F06.
Figure 21:
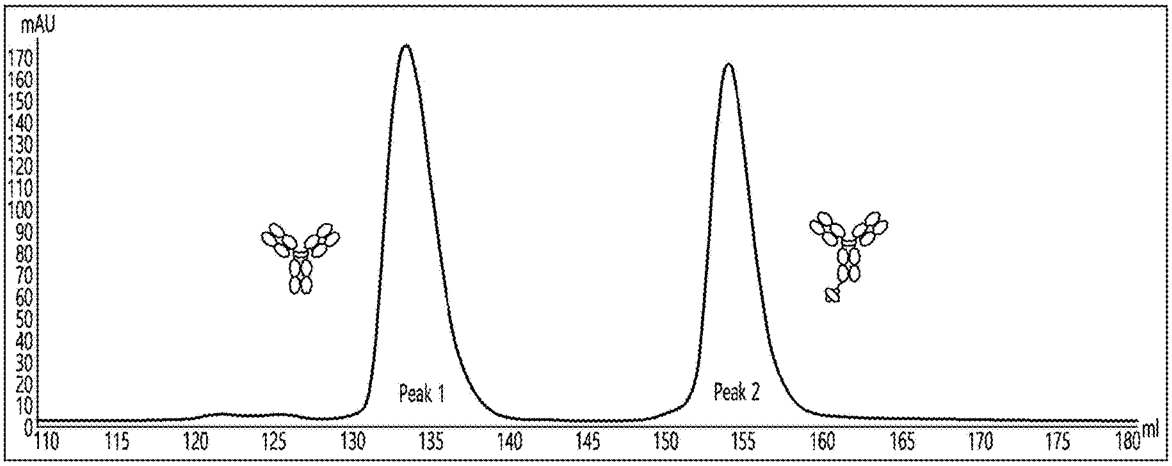
FIG. 21 shows the purification profile of affinity chromatography using POROS MabCapture A Select resin applied on a bioactive peptide mixture containing anti-BACE and anti-BACE-F06.

As a result of applying the pH gradient of the elution buffer, two peaks appeared as shown in FIGS. 20 and 21. Specifically, at a relatively high pH, a monospecific antibody having no VH3 domains (zero) was eluted first (Peak 1), and as the pH was lowered, a monovalent bispecific antibody having one VH3 domains was eluted (Peak 2). These results were reconfirmed from the SE-HPLC and SDS-PAGE results shown in FIGS. 22 to 25.

Example 5-3. Fc-scFv (VH3+)

The resolution of the sample was confirmed using the protein A resin used in Example 3. All protein A resins having the confirmed resolution shown in Table 5 may be used as the protein A resin. As an example, POROS Mab-Capture A Select (Thremo Fisher SCIENTIFIC, Cat. No. A26458) was used for purification. As a sample for purification, Fc and Fc-scFv (F06) from which Fab had been removed by treating a monospecific antibody (hu11F11) and a monovalent bispecific antibody (hu11F11-F06) with papain were prepared. Specifically, papain was diluted with digestion buffer (10 mM PBS, 20 mM EDTA, 10 mM cysteine-HCl, and pH 7.4), and mixed with the prepared sample at the ratio of 1:100 (papain:antibody), and the mixture was caused to react at a temperature of 37° C. for 4 hours.

Figure 26:
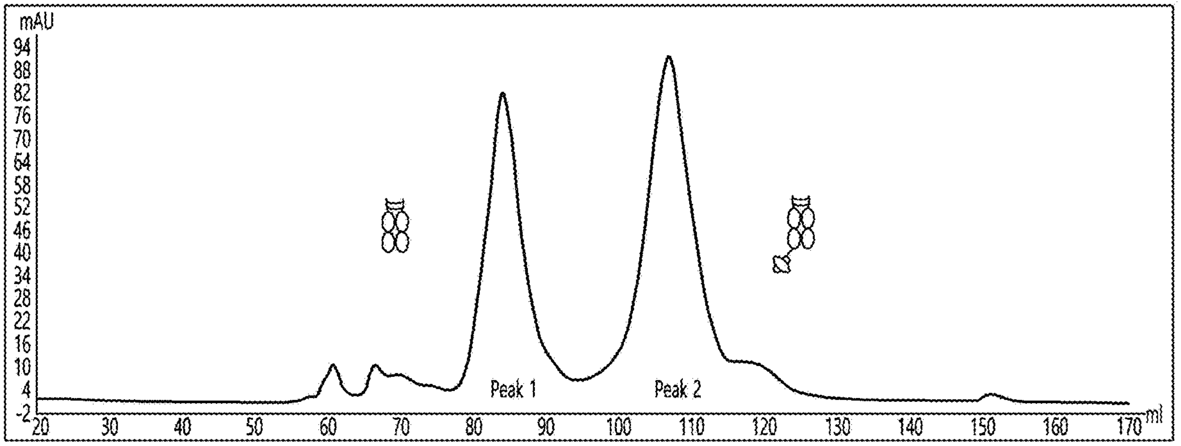
FIG. 26 shows the purification profile of affinity chromatography using POROS MabCapture A Select resin applied on a bioactive peptide mixture containing Fc and Fc-F06.
Figure 27:
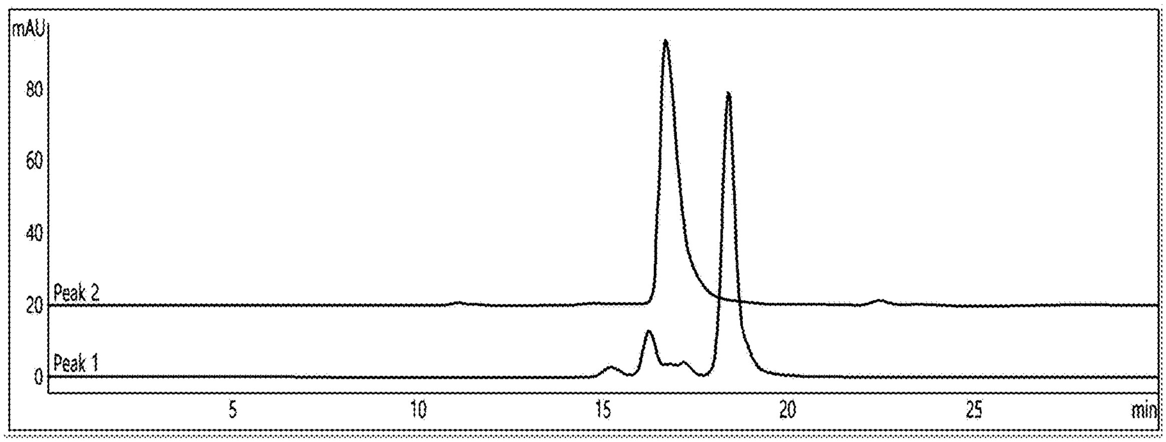
FIG. 27 shows SE-HPLC analysis of the purification results obtained by applying a POROS MabCapture A Select resin on a bioactive peptide mixture including Fc and Fc-F06.
Figure 28:
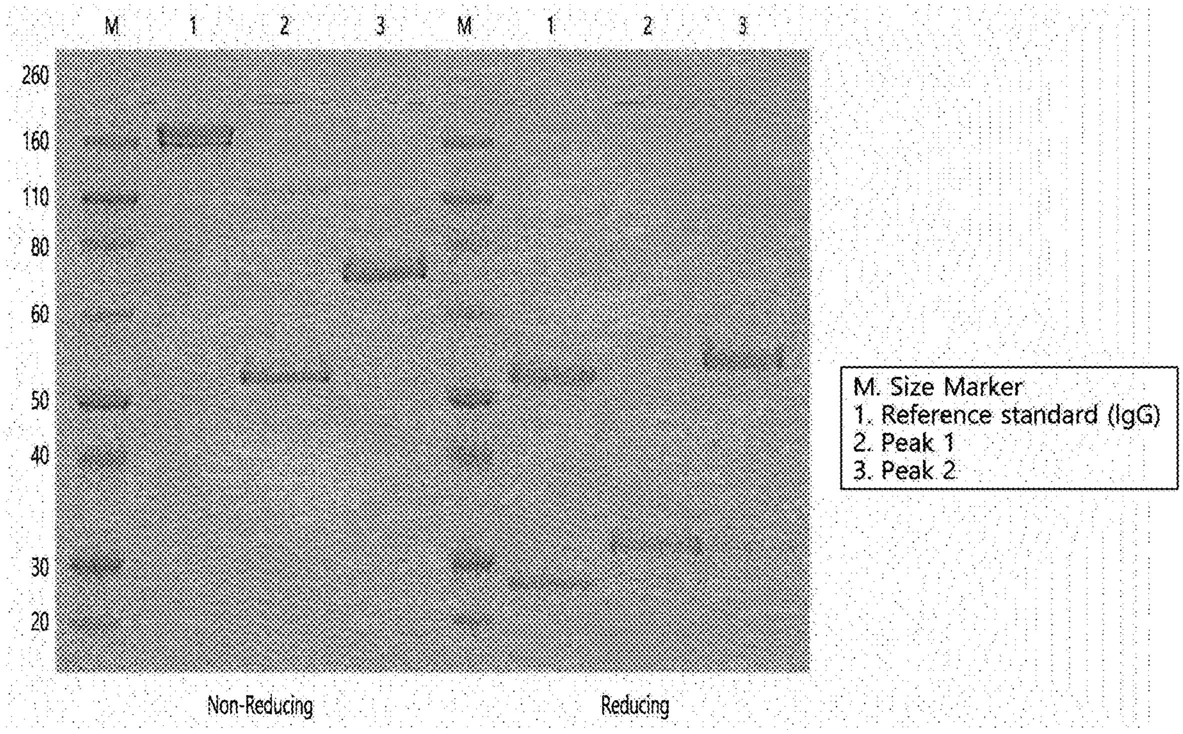
FIG. 28 shows SDS-PAGE analysis of the purification results obtained by applying a POROS MabCapture A Select resin on a bioactive peptide mixture including Fc and Fc-F06.

After equilibration using an equilibration buffer (25 mM citrate/25 mM sodium phosphate, pH 7.0), the sample was loaded into the column. An elution buffer (25 mM citrate/25 mM sodium phosphate, pH 2.5) was used, and a residence time was 6 minutes, and wash conditions included 0%>50%/1 column volume elution buffer and the pH of 7.0 to 5.0. The gradient condition was 50%>100%/30 column volume of elution buffer. FIG. 26 shows the purification profile of affinity chromatography, and SE-HPLC and SDS-PAGE results are shown in FIGS. 27 and 28, respectively.

As a result of applying the pH gradient of the elution buffer, two peaks appeared as shown in FIG. 26. A typical antibody has Fab connected to the N-terminus of Fc, whereas the sample separated in this example does not contain Fab at the N-terminus of Fc. Nevertheless, according to FIG. 26, at a relatively high pH, Fc without a VH3 domain (zero) was eluted first (Peak 1), and as the pH decreased, Fc-scFv (F06) having one VH3 domain was eluted (Peak 2). These results were reconfirmed from the SE-HPLC and SDS-PAGE results shown in FIGS. 27 and 28. This result suggests that the purification method according to the present disclosure is used not only for the purification of an antibody, but also for the purification of various Fc-containing peptides having a difference in the number of VH3 domains, for example, various peptides containing Fc-scFv (for example, Fc-scFv connected to a drug or a functional peptide).

Example 5-4. GLP-1-Fc-scFv (VH3+)

The resolution of the sample was confirmed using the protein A resin used in Example 3. All protein A resins having the confirmed resolution shown in Table 5 may be used as the protein A resin. As an example, POROS Mab-Capture A Select (Thremo Fisher SCIENTIFIC, Cat. No. A26458) was used for purification. As a sample for purification, a mixture including GLP-1-Fc (F06) and GLP-1-Fc-scFv (F06) having one VH3 domain was prepared in the same manner as used in Example 1, except that instead of Fab, the known sequence of GLP-1 (Glucagon-like Peptide-1) was connected to Fc. GLP-1 used in this example is a kind of peptide drug, and research and clinical studies thereinto are being actively conducted in relation to diseases such as diabetes and Alzheimer's. In the present example, it was tested whether separation according to the number of VH3 domains can be made even when such a peptide drug is included.

Figure 29:
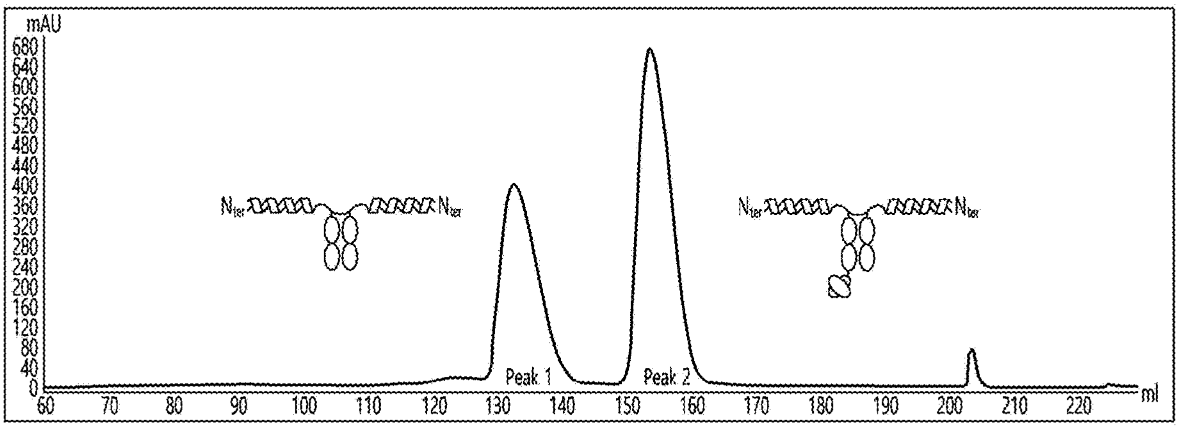
FIG. 29 shows the purification profile of affinity chromatography using POROS MabCapture A Select resin applied on a bioactive peptide mixture containing GLP-1-Fc and GLP-1-Fc-F06.
Figure 30:
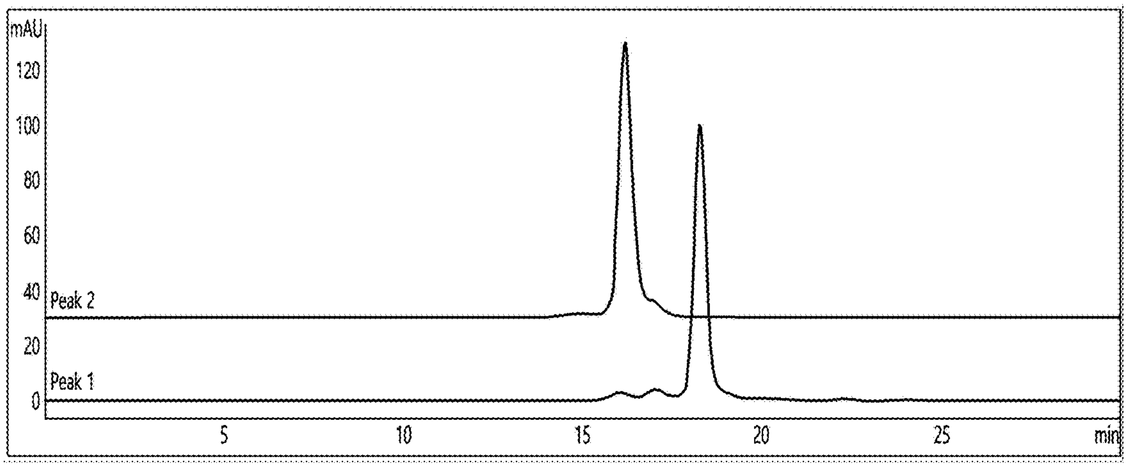
FIG. 30 shows SE-HPLC analysis of the purification results obtained by applying a POROS MabCapture A Select resin on a bioactive peptide mixture including GLP-1-Fc and GLP-1-Fc-F06.

After equilibration using an equilibration buffer (25 mM citrate/25 mM sodium phosphate, pH 7.0), the sample was loaded into the column. An elution buffer (25 mM citrate/25 mM sodium phosphate, pH 2.5) was used, and a residence time was 6 minutes, and wash conditions included 0%>50%/1 column volume elution buffer and the pH of 7.0 to 5.0. The gradient condition was 50%>100%/30 column volume of elution buffer. FIG. 29 shows the purification profile of affinity chromatography, and FIG. 30 shows SE-HPLC results.

As a result of applying the pH gradient of the elution buffer, two peaks appeared as shown in FIG. 29. A typical antibody has Fab connected to the N-terminus of Fc, whereas the sample separated in this example is a fusion protein and contains GLP-1, instead of Fab, at the N-terminus of Fc. Nevertheless, according to FIG. 29, at a relatively high pH, GLP-1-Fc without a VH3 domain (zero) was eluted first (Peak 1), and as the pH decreased, GLP-1-Fc-scFv (F06) having one VH3 domain was eluted (Peak 2). These results were reconfirmed from the SE-HPLC results shown in FIG. 30. This result suggests that the purification method according to the present disclosure is used not only for the purification of an antibody, but also for the separation of various Fc-containing peptides having a difference in the number of VH3 domains, for example, bioactive peptides including, in addition to the components of an antibody, other active ingredients.

The pH concentration gradient of the elution buffer in Examples 5-1 to 5-4 is as shown in Table 6.

TABLE 6

| Example | Peak 1 start pH | Peak 1 End pH | Peak 2 start pH | Peak 2 End pH |
|---|---|---|---|---|
| Example 5-1 (hu11F11 & hu11F11-scFv) | 3.51 | 3.41 | 3.41 | 3.32 |
| Example 5-2 (ch1E4 & ch1E4-scFv) | 4.23 | 4.08 | 3.96 | 3.76 |
| Example 5-2 (anti-BACE & Anti-BACE-scFv) | 4.05 | 3.89 | 3.73 | 3.57 |
| Example 5-3 (Fc & Fc-scFv) | 3.98 | 3.78 | 3.78 | 3.53 |
| Example 5-4 (GLP-1-Fc & GLP-1-Fc-scFv) | 4.17 | 3.95 | 3.83 | 3.61 |

Example 5-5. IgG(VH3(±))-scFv(VH3+)

The resolution of the sample was confirmed using the protein A resin used in Example 3. All protein A resins having the confirmed resolution shown in Table 5 may be used as the protein A resin. As an example, POROS Mab-Capture A Select (Thremo Fisher SCIENTIFIC, Cat. No. A26458) was used for purification. As a sample for the purification, a mixture comprising 4 types of antibodies, including monospecific antibody having two VH3 domains (hu11F11) and monovalent bispecific antibody having three VH3 domains (hu11F11-F06), both of which are prepared by the method of Example 1, and monospecific antibody having no VH3 domain (anti-BACE) and monovalent bispecific antibody having one VH3 domain (anti-BACE-F06), both of which are prepared by the same method of Example 1 except using anti-BACE antibody that does not contain VH3 domain in the variable region of IgG, was used.

Figure 31:
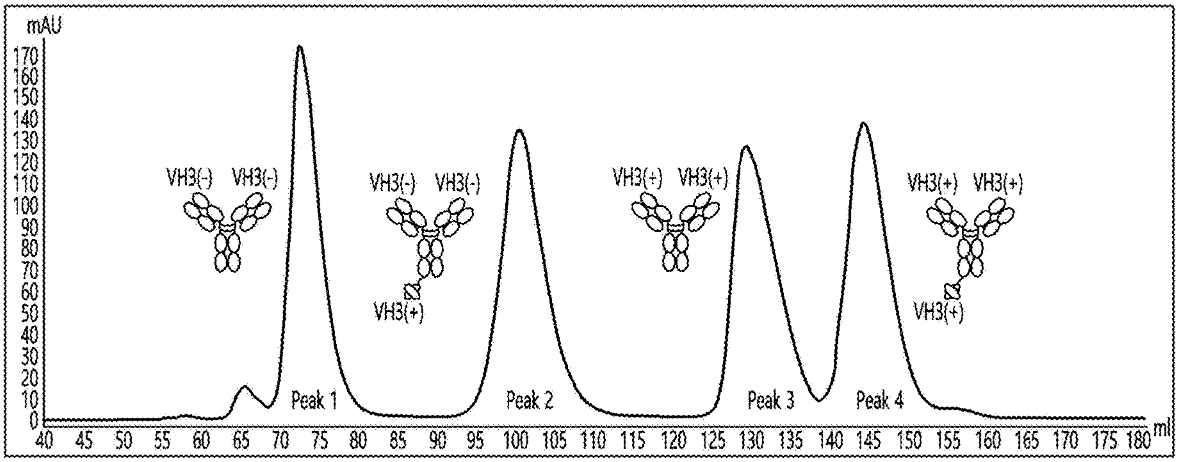
FIG. 31 shows the purification profile of affinity chromatography using a POROS MabCapture A Select resin applied on a sample containing anti-BACE, anti-BACE-F06, hu11F11, and hu11F11-F06.
Figure 32:
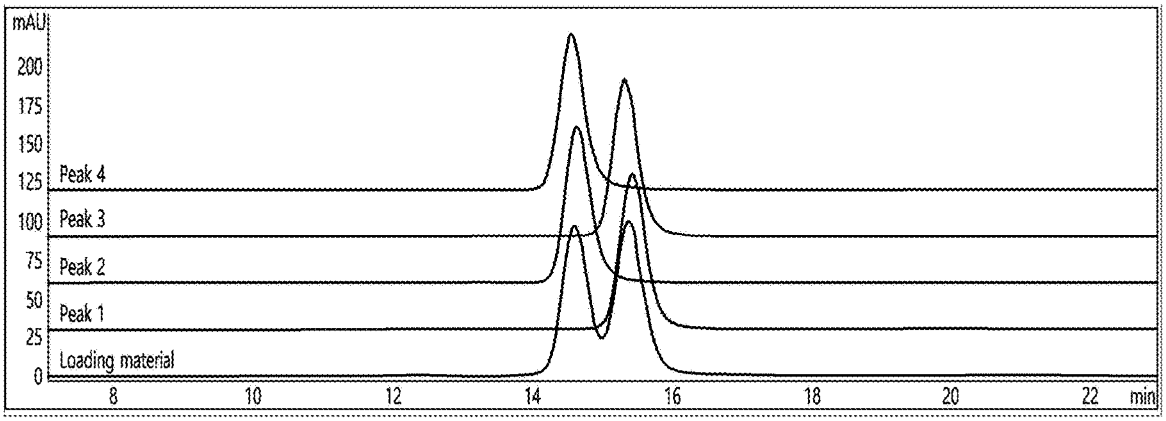
FIG. 32 shows SE-HPLC analysis of the purification results obtained by applying a POROS MabCapture A Select resin on a sample containing anti-BACE, anti-BACE-F06, hu11F11, and hu11F11-F06.
Figures 33, 34:
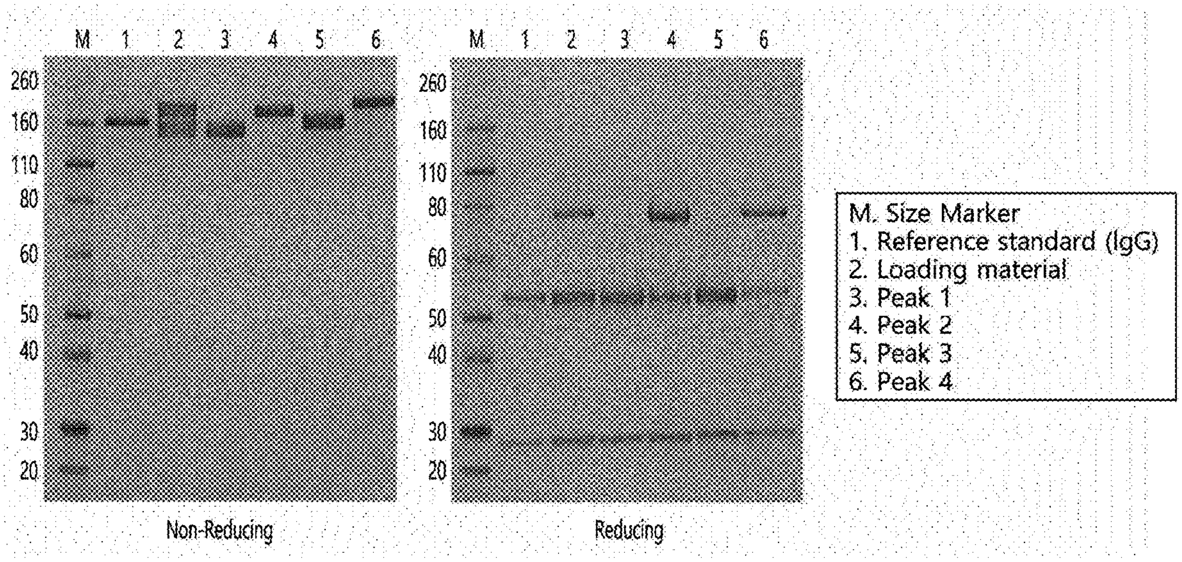
FIG. 33 shows SDS-PAGE analysis of the purification results obtained by applying a POROS MabCapture A Select resin on a sample containing anti-BACE, anti-BACE-F06, hu11F11, and hu11F11-F06.
FIG. 34 shows LC/MS analysis of the purification results obtained by applying a POROS MabCapture A Select resin on a sample containing anti-BACE, anti-BACE-F06, hu11F11, and hu11F11-F06.

After equilibration using an equilibration buffer (25 mM citrate/25 mM sodium phosphate, pH 7.0), the sample was loaded into the column. An elution buffer (25 mM citrate/25 mM sodium phosphate, pH 2.5) was used, and a residence time was 6 minutes, and wash conditions included 0%>50%/1 column volume elution buffer and the pH of 7.0 to 5.0. The gradient condition was 50%>100%/30 column volume of elution buffer. FIG. 31 shows the purification profile of affinity chromatography, and SE-HPLC, SDS-PAGE, and LC/MS results are shown in FIGS. 32 to 34, respectively.

As a result of applying the pH gradient of the elution buffer, four peaks appeared as shown in FIG. 31, and the peaks of the peptides (anti-BACE antibody: 0, anti-BACE-F06: 1, The peaks of hu11F11 antibody: 2, hu11F11-F06: 3) were clearly separated, confirming that a target peptide could be selectively purified. In addition, these results were reconfirmed from the SE-HPLC, SDS-PAGE and LC/MS results of FIGS. 32 to 34. From this, it was confirmed that the separation method of the present application can purify peptides very precisely according to the number of VH3 domains included in each peptide.

Example 5-6. IgG(VH3(±))-scFv(VH3+)

The resolution of the sample was confirmed using the protein A resin used in Example 3. All protein A resins having the confirmed resolution shown in Table 5 may be used as the protein A resin. As an example, POROS Mab-Capture A Select (Thremo Fisher SCIENTIFIC, Cat. No. A26458) was used for purification. As a sample for the purification, a mixture comprising 4 types of antibodies, including monospecific antibody having two VH3 domains (hu11F11) and monovalent bispecific antibody having three VH3 domains (hu11F11-F06), both of which are prepared by the method of Example 1, and monospecific antibody having no VH3 domain (ch1E4) and monovalent bispecific antibody having one VH3 domain (ch1E4-F06), both of which are prepared by the same method of Example 1 except using ch1E4 antibody that does not contain VH3 domain in the variable region of IgG, was used.

Figure 35:
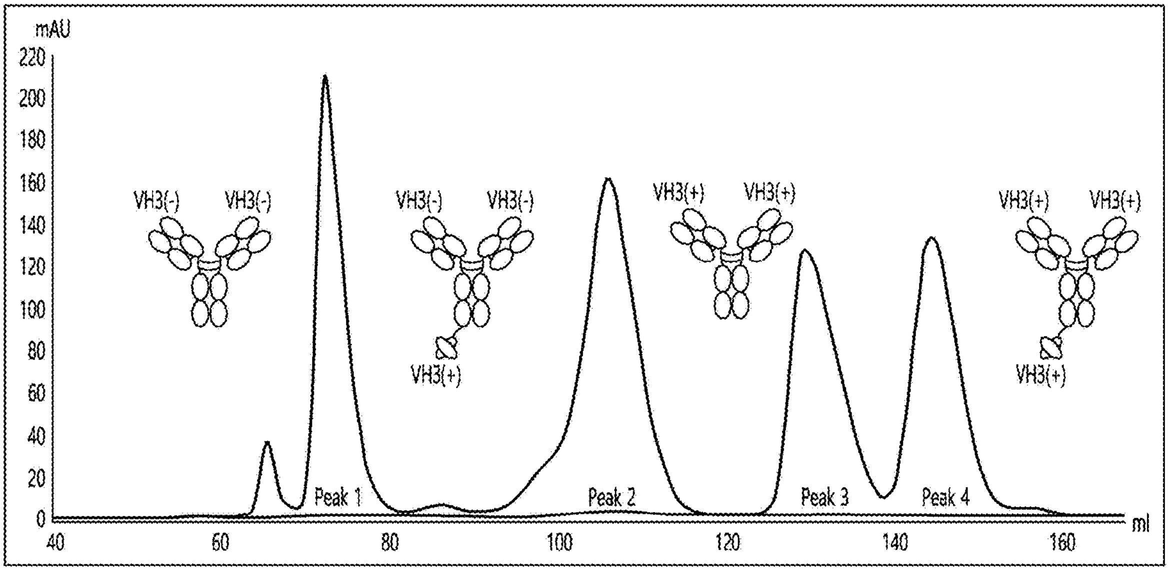
FIG. 35 shows the purification profile of affinity chromatography using a POROS MabCapture A Select resin applied on a sample containing ch1E4, ch1E4-F06, hu11F11, and hu11F11-F06.

After equilibration using an equilibration buffer (25 mM citrate/25 mM sodium phosphate, pH 7.0), the sample was loaded into the column. An elution buffer (25 mM citrate/25 mM sodium phosphate, pH 2.5) was used, and a residence time was 6 minutes, and wash conditions included 0%>50%/1 column volume elution buffer and the pH of 7.0 to 5.0. The gradient condition was 50%>100%/30 column volume of elution buffer. FIG. 35 shows the purification profile of affinity chromatography.

As a result of applying the pH gradient of the elution buffer, four peaks appeared as shown in FIG. 35, and the peaks of the peptides (ch1E4: 0, ch1E4-F06: 1; hu11F11: 2, hu11F11-F06: 3) were clearly separated, confirming that a target peptide could be selectively purified according to the number of VH3 domains.

The invention claimed is:

1. A method of purifying an fragment crystallizable (Fc)-containing bioactive peptide, the method comprising:

(a) loading a mixture of Fc-containing bioactive peptides into a column including an affinity matrix containing protein A ligand, wherein the mixture of Fc-containing bioactive peptides includes a first Fc-containing bioactive peptide and a second Fc-containing bioactive peptide, and the second Fc-containing bioactive peptide includes at least one more human heavy chain variable region 3 (VH3) domain, compared to the first Fc-containing bioactive peptide; and (b) loading an eluate into the column to separate and elute the Fc-containing bioactive peptides at different pHs depending on the number of human VH3 domains included in each of the Fc-containing bioactive peptides that are included in the mixture of Fc-containing bioactive peptides, wherein the first Fc-containing bioactive peptide includes n human VH3 domains, and n is an integer greater than or equal to 0.

2. The method of claim 1, wherein the mixture of Fc-containing bioactive peptides further comprises a third Fc-containing bioactive peptide which includes at least one more human VH3 domain, compared to the second Fc-containing bioactive peptide.

3. The method of claim 2, wherein in the mixture of Fc-containing bioactive peptide, the first Fc-containing bioactive peptide includes n human VH3 domains (n is an integer greater than or equal to 0), the second Fc-containing bioactive peptide includes n+1 human VH3 domains, and the third Fc-containing bioactive peptide includes n+2 human VH3 domains.

4. The method of claim 1, wherein the process (b) comprises:

(b1) eluting the first Fc-containing bioactive peptide by loading an eluate having a first pH range into the column; and (b2) eluting the second Fc-containing bioactive peptide by loading an eluate having a second pH range lower than the first pH range into the column.

5. The method of claim 2, wherein the process (b) comprises:

(b1) eluting the first Fc-containing bioactive peptide by loading an eluate having a first pH range into the column;

(b2) eluting the second Fc-containing bioactive peptide by loading an eluate having a second pH range lower than the first pH range into the column; and (b3) eluting the third Fc-containing bioactive peptide by loading an eluate having a third pH range lower than the second pH range into the column.

6. The method of claim 1, wherein each Fc-containing bioactive peptide included in the mixture comprises an Fc to which a mutation affecting binding to wild-type protein A is not introduced.

7. The method of claim 1, wherein when the first Fc-containing bioactive peptide or the second Fc-containing bioactive peptide includes a VH3 domain, the first Fc-containing bioactive peptide and the second Fc containing bioactive peptide each include a VH domain-containing variable region sequence selected from the following sequences:

a heavy chain variable region sequence of SEQ ID No. 1 and a light chain variable region sequence of SEQ ID No. 2;

a heavy chain variable region sequence of SEQ ID No. 3 and a light chain variable region sequence of SEQ ID No. 4;

a heavy chain variable region sequence of SEQ ID No. 5 and a light chain variable region sequence of SEQ ID No. 6;

a heavy chain variable region sequence of SEQ ID No. 7 and a light chain variable region sequence of SEQ ID No. 8; and a heavy chain variable region sequence of SEQ ID No. 9 and a light chain variable region sequence of SEQ ID No. 10.

8. The method of claim 2, wherein the third Fc-containing bioactive peptide includes a VH domain-containing variable region sequence selected from the following sequences:

a heavy chain variable region sequence of SEQ ID No. 1 and a light chain variable region sequence of SEQ ID No. 2;

a heavy chain variable region sequence of SEQ ID No. 3 and a light chain variable region sequence of SEQ ID No. 4;

a heavy chain variable region sequence of SEQ ID No. 5 and a light chain variable region sequence of SEQ ID No. 6;

a heavy chain variable region sequence of SEQ ID No. 7 and a light chain variable region sequence of SEQ ID No. 8; and a heavy chain variable region sequence of SEQ ID No. 9 and a light chain variable region sequence of SEQ ID No. 10.

9. The method of claim 1, wherein the Fc-containing bioactive peptide is an antibody containing immunoglobulin G (IgG).

10. The method of claim 1, wherein the Fc-containing bioactive peptide is an IgG-single chain variable fragment (scFv) bispecific antibody.

11. The method of claim 1, wherein the Fc-containing bioactive peptide comprises a peptide drug bound to Fc.

12. The method of claim 11, wherein the peptide drug comprises at least one selected from the group consisting of hormones, cytokines, enzymes, antibodies, growth factors, transcriptional regulators, blood factors, vaccines, structural proteins, ligand proteins, and receptors.

13. The method of claim 2, wherein the first Fc-containing bioactive peptide does not include scFv;

the second Fc-containing bioactive peptide includes one scFv consisting of SEQ ID No. 11, connected to the C-terminus of one of two heavy chains of Fc; and the third Fc-containing bioactive peptide includes two scFv each consisting of SEQ ID No. 11, respectively connected to the C-termini of two heavy chains of Fc.

14. The method of claim 1, wherein the Fc-containing bioactive peptide is IgG, and a variable region of the IgG antibody comprises a human VH3 domain.

15. The method of claim 2, wherein the mixture of Fc-containing bioactive peptides comprises:

(a) a monospecific antibody corresponding to the first Fc-containing bioactive peptide;

(b) a monovalent bispecific antibody corresponding to the second Fc-containing bioactive peptide in which one antigen-binding fragment including a human VH3 domain binds to the C-terminus of any one of two heavy chain constant regions of the monospecific antibody; and (c) a bivalent bispecific antibody corresponding to a third Fc-containing bioactive peptide in which the antigen-binding fragment binds to the C-terminus of each of two heavy chain constant regions of the monospecific antibody, wherein:

(a) the monospecific antibody is eluted at a first pH range;

(b) the monovalent bispecific antibody is eluted at a second pH range lower than the first pH range; and (c) the bivalent bispecific antibody is eluted at a third pH range lower than the second pH range.

16. The method of claim 15, wherein a variable region of the monospecific antibody comprises a human VH3 domain.

17. The method of claim 15, wherein a variable region of the monospecific antibody does not include a human VH3 domain.

18. The method of claim 15, wherein the antigen-binding fragment is scFv including an amino acid sequence of SEQ ID No. 11.

19. The method of claim 15, wherein the first pH range is 3.4 or more and 5.0 or less, the second pH range is 3.3 or more and 4.1 or less, and the third pH range is 3.0 or more and 4.0 or less.

* * * * *